United States Patent
Masuda

(10) Patent No.: US 8,048,074 B2
(45) Date of Patent: Nov. 1, 2011

(54) SURGICAL OPERATING APPARATUS

(75) Inventor: Shinya Masuda, Hino (JP)

(73) Assignee: Olympus Medical Systems Corp. (JP)

( * ) Notice: Subject to any disclaimer, the term of this patent is extended or adjusted under 35 U.S.C. 154(b) by 863 days.

(21) Appl. No.: 12/057,490

(22) Filed: Mar. 28, 2008

(65) Prior Publication Data

US 2009/0248051 A1    Oct. 1, 2009

(51) Int. Cl.
*A61B 18/18* (2006.01)
(52) U.S. Cl. .......................... 606/51; 606/169
(58) Field of Classification Search .............. 606/39, 606/167, 169, 48, 45, 49–52, 190, 205; 604/22; 433/86, 119; 600/437; 601/2
See application file for complete search history.

(56) References Cited

U.S. PATENT DOCUMENTS

| | | | | |
|---|---|---|---|---|
| 6,056,735 | A * | 5/2000 | Okada et al. ........................ | 606/1 |
| 2004/0199194 | A1* | 10/2004 | Witt et al. ....................... | 606/169 |
| 2006/0259054 | A1* | 11/2006 | Masuda et al. ................ | 606/169 |
| 2008/0132887 | A1* | 6/2008 | Masuda et al. .................. | 606/37 |

FOREIGN PATENT DOCUMENTS

| | | |
|---|---|---|
| CN | 101099691 A | 1/2008 |
| EP | 1 875 875 | 1/2008 |
| JP | 2007-50181 | 3/2007 |
| JP | 2008-11987 | 1/2008 |

OTHER PUBLICATIONS

Letter from German associate dated Jun. 8, 2009 forwarding the Search Report dated Jun. 3, 2009 to Japanese associate, including discussion of relevancy thereof.
Search Report issued by European Patent Office in connection with corresponding application No. EP 09 00 4507 on Jun. 3, 2009.
Office Action issued by the Chinese Patent Office on Jun. 1, 2010 in connection with corresponding Chinese Patent Application No. 200910131948.X.
English translation of Chinese Office Action issued in connection with Chinese Patent Application No. 200910131948.X on Jun. 1, 2010.

* cited by examiner

*Primary Examiner* — Amy Lang
(74) *Attorney, Agent, or Firm* — Ostrolenk Faber LLP

(57) ABSTRACT

A surgical operating apparatus includes an ultrasonic treatment section which performs ultrasonic treatment on a living tissue, and a high-frequency treatment section which performs high-frequency treatment on the living tissue, and includes a narrow width part which is provided on at least one of mutually opposed surfaces of a first electrode portion of a first grasping member and a second electrode portion of a second grasping member. The narrow width part is configured to be disposed at a position where the second grasping member does not easily suffer a stress due to ultrasonic vibration when the living tissue is grasped between the second grasping member and the first grasping member, and to make a distance between the mutually opposed surfaces of the first electrode portion and the second electrode portion narrower than a distance at other positions.

9 Claims, 16 Drawing Sheets

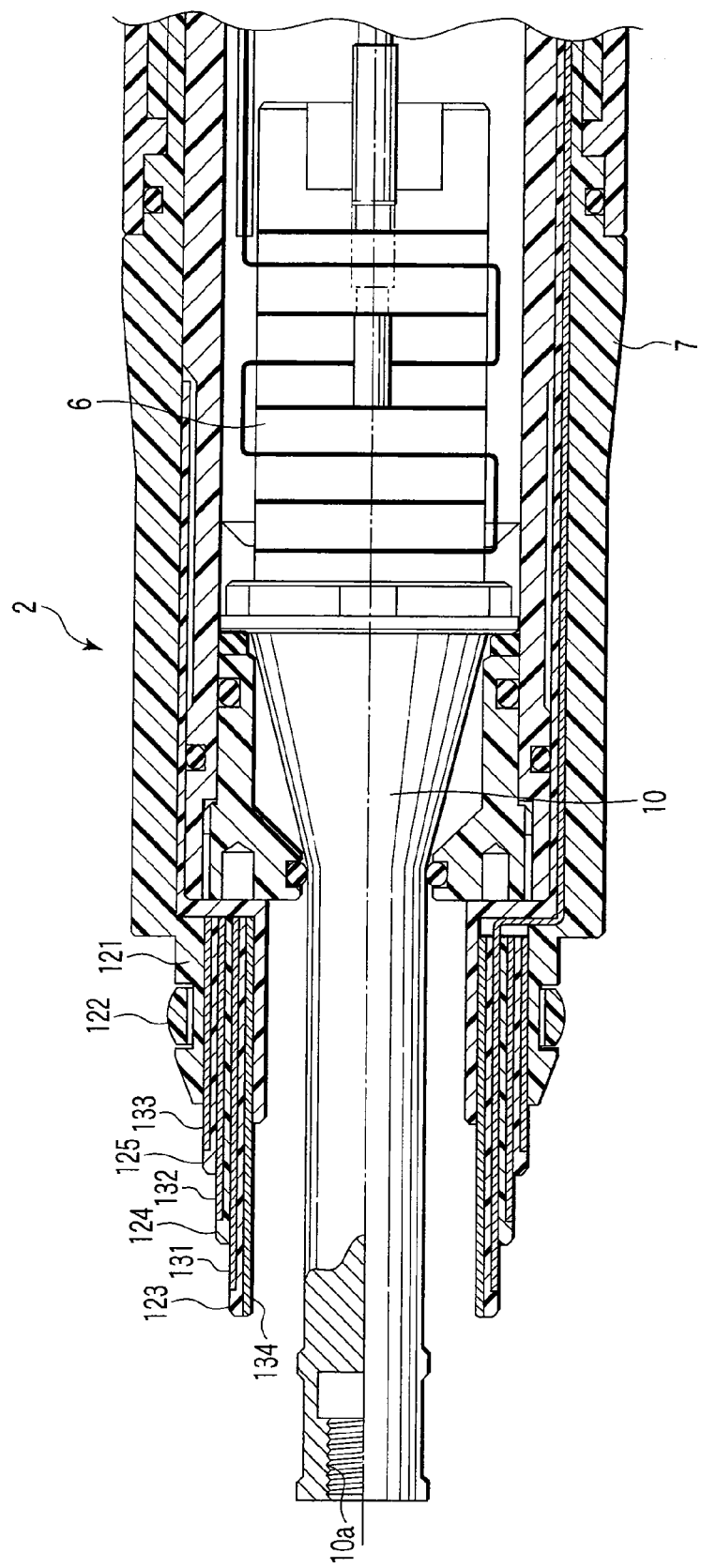
F I G. 4

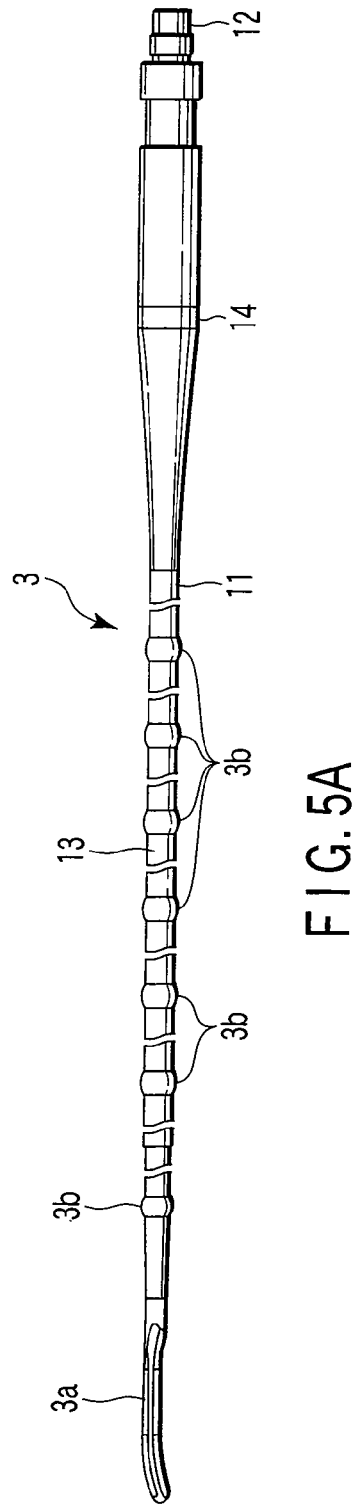
F I G. 5A
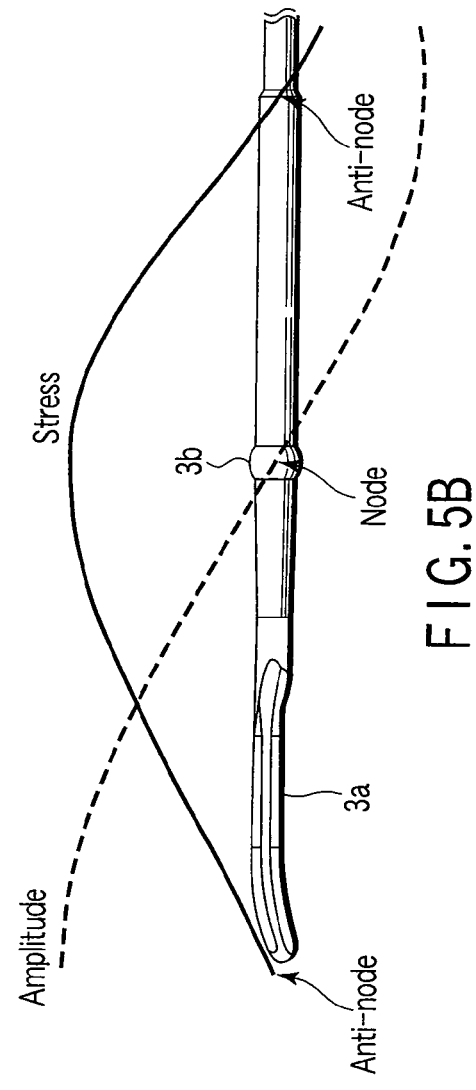
F I G. 5B

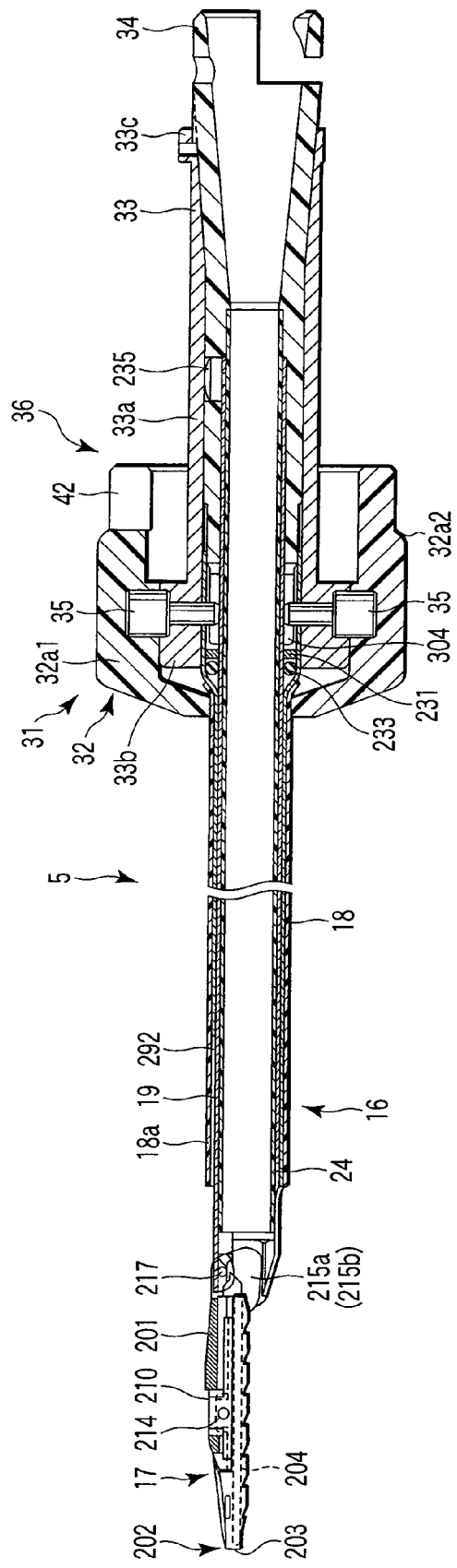
F I G. 6

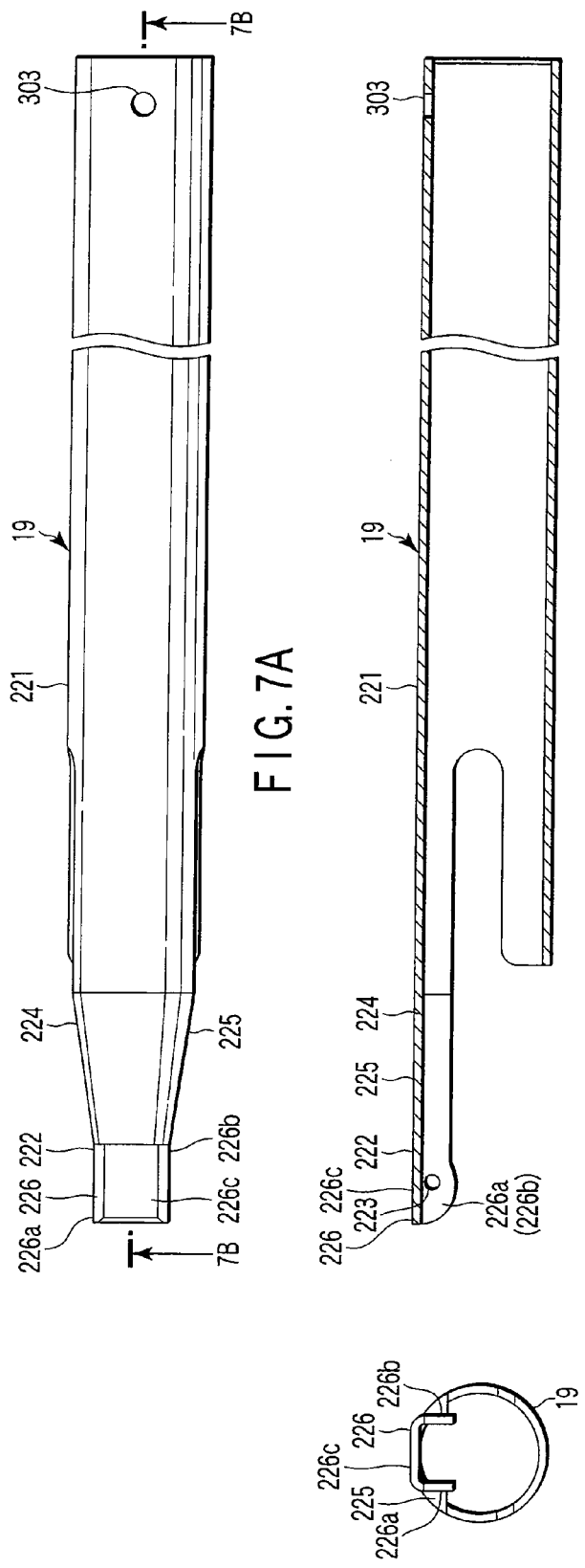
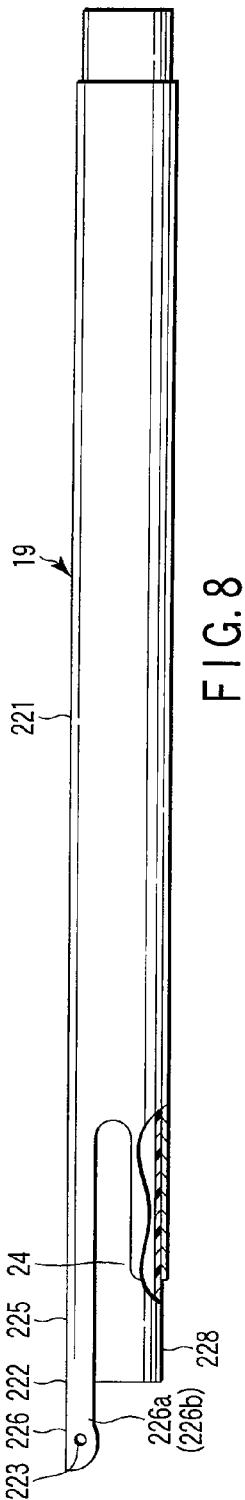
FIG. 7A
FIG. 7B
FIG. 7C
FIG. 8

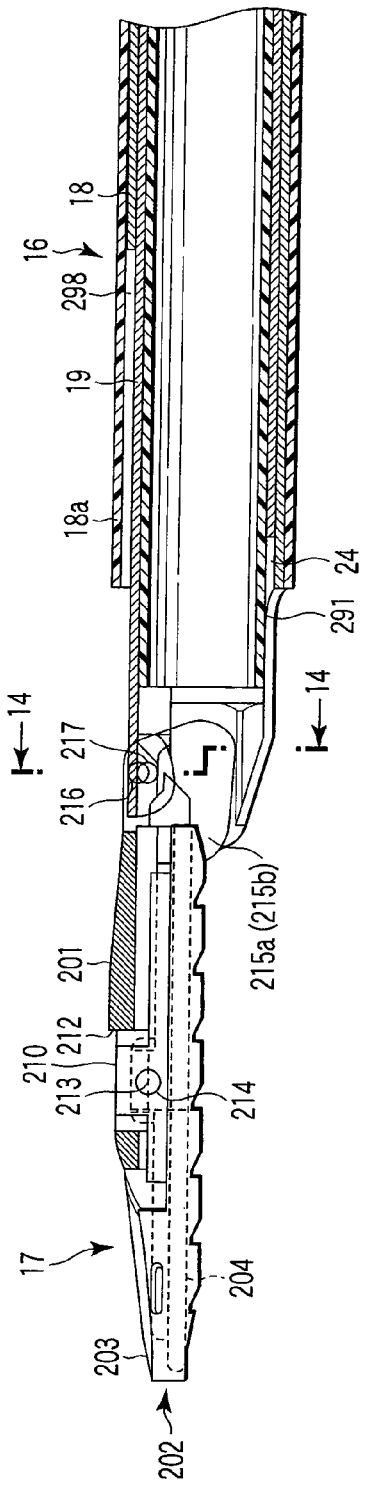
F I G. 13
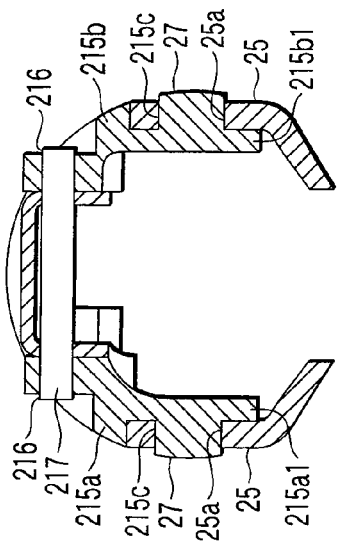
F I G. 14

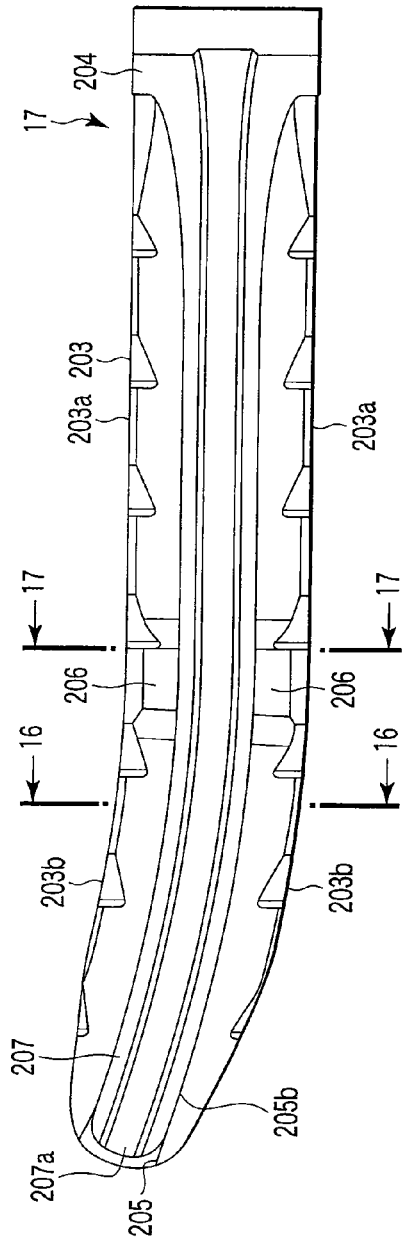
FIG. 15
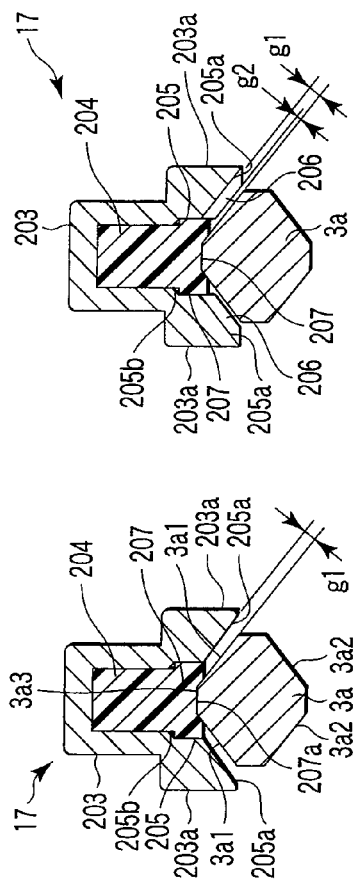
FIG. 16
FIG. 17

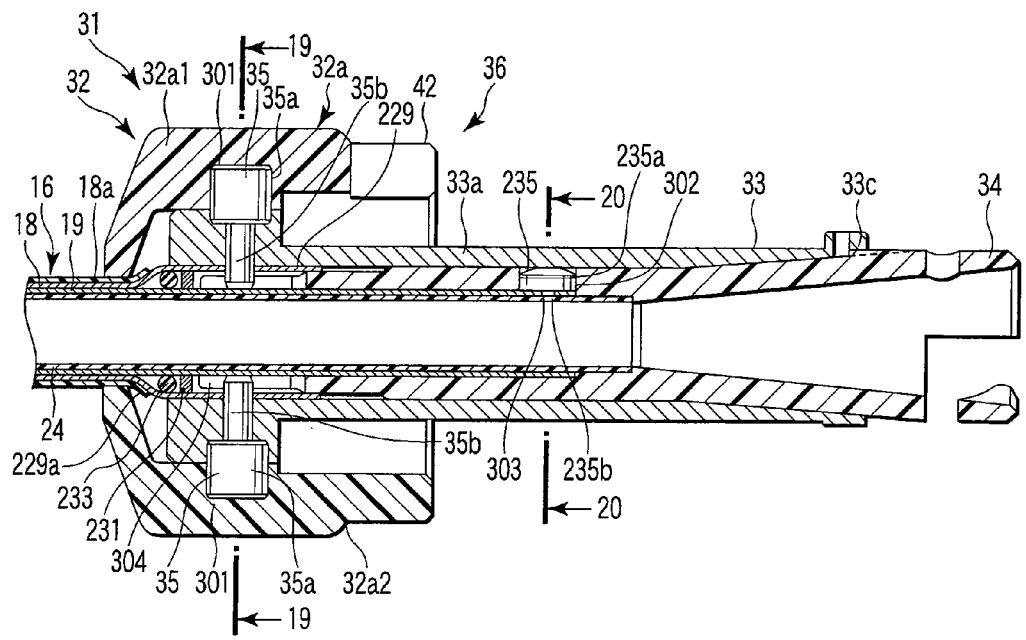
FIG. 18
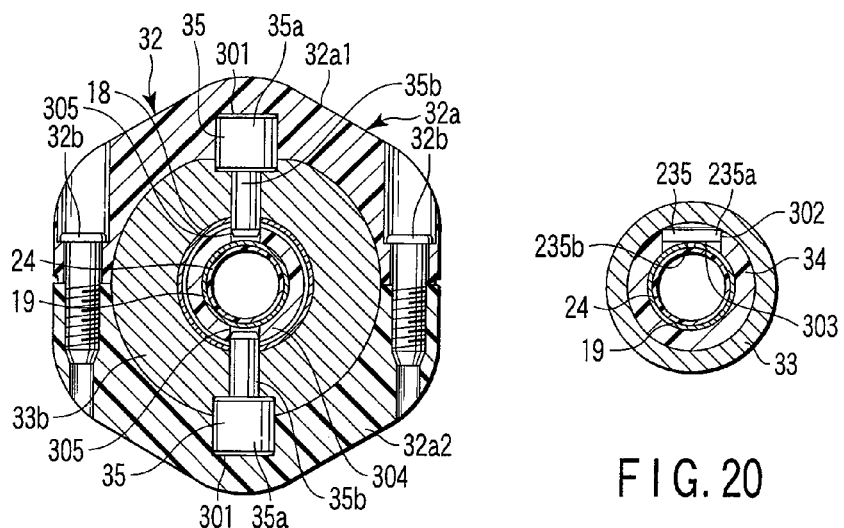
FIG. 19
FIG. 20

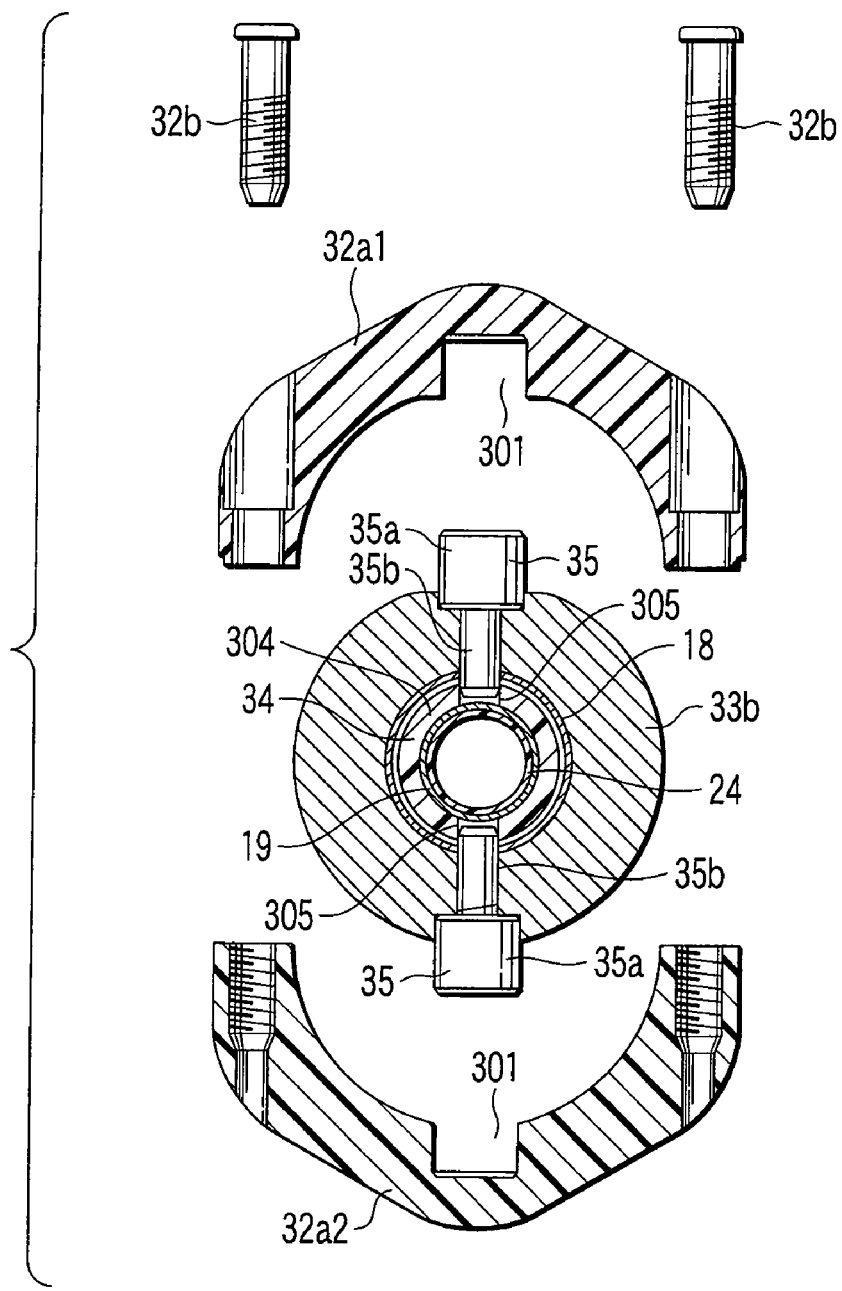
F I G. 21

SURGICAL OPERATING APPARATUS

BACKGROUND OF THE INVENTION

The present invention relates to a surgical operating apparatus which can perform therapeutic treatment, such as incision, resection or coagulation, of a living tissue by making use of composite energy of ultrasonic and high-frequency waves, and can also perform therapeutic treatment by making use of high-frequency waves.

Jpn. Pat. Appln. KOKAI Publication No. 2007-50181 (patent document 1) and Jpn. Pat. Appln. KOKAI Publication No. 2008-11987 (patent document 2), for instance, disclose general examples of an ultrasonic operating apparatus which can perform therapeutic treatment, such as incision, resection or coagulation, of a living tissue by making use of ultrasonic and can also perform therapeutic treatment by high-frequency waves.

In this apparatus, a proximal-side operation section is coupled to a proximal end portion of an elongated insertion section. An ultrasonic transducer which generates ultrasonic vibration is provided in the operation section. A treatment section for treating a living tissue is provided at a distal end portion of the insertion section.

The insertion section has an elongated circular tubular sheath. A rod-shaped vibration transmission member (probe) is inserted in the sheath. A proximal end portion of the vibration transmission member is detachably attached to the ultrasonic transducer via a screw-type coupling section. Ultrasonic vibration, which is generated by the ultrasonic transducer, is transmitted to a probe distal end portion at the distal end side of the vibration transmission member.

In the treatment section, a jaw is disposed to be opposed to the probe distal end portion. A proximal end portion of the jaw is rotatably supported on a distal end portion of the sheath via a support shaft. A driving member for driving the jaw is inserted in the sheath so as to be axially advancible/retreatable. A proximal end portion of a jaw body is coupled to a distal end portion of the driving member via a coupling pin.

The operation section is provided with an operation handle. In accordance with the operation of the operation handle, the driving member is axially advanced/retreated. In interlock with the operation of the driving member, the jaw is opened/closed relative to the probe distal end portion.

At this time, a living tissue is held between the probe distal end portion and the jaw in accordance with the closing operation of the jaw. In this state, ultrasonic vibration from the ultrasonic transducer is transmitted to the probe distal end portion on the treatment section side via the vibration transmission member. Thereby, using ultrasonic wave, therapeutic treatment, such as incision, resection or coagulation, of the living tissue is performed.

Electrodes for high-frequency treatment are formed on the probe distal end portion and the jaw. A high-frequency current is supplied, as needed, to at least one of the probe distal end portion and the jaw of the treatment section.

As shown in FIG. 26, there is a case in which the probe distal end portion is formed in a substantially J-shaped curved shape in accordance with an object of therapeutic treatment. FIG. 26 shows a distribution of a stress acting in the probe distal end portion. In the probe distal end portion of such a curved shape, a stress due to ultrasonic vibration tends to concentrate at a proximal end side position of the curved shape, as indicated by an arrow P in FIG. 26.

BRIEF SUMMARY OF THE INVENTION

According to an aspect of the present invention, there is provided a surgical operating apparatus including an ultrasonic treatment section which performs ultrasonic treatment on a living tissue, and a high-frequency treatment section which performs high-frequency treatment on the living tissue, wherein the ultrasonic treatment section comprises: a first grasping member; a second grasping member which is provided to be openable/closable relative to the first grasping member, the living tissue being grasped between the first grasping member and the second grasping member; an ultrasonic vibration portion which is provided in the first grasping member and is connected to an ultrasonic transducer; and a push portion which is provided on the second grasping member, is opposed to the ultrasonic vibration portion, and pushes the living tissue between the push portion and the ultrasonic vibration portion, the ultrasonic treatment section performs the ultrasonic treatment on the living tissue between the ultrasonic vibration portion and the push portion, and the high-frequency treatment section comprises: a first electrode portion which is provided on the first grasping member; a second electrode portion which is provided on the second grasping member, and is opposed to the first grasping member, the living tissue, which is grasped between the second electrode portion and the first grasping member, being subjected to treatment between the second electrode portion and the first electrode portion; and a narrow width part which is provided on at least one of mutually opposed surfaces of the first electrode portion and the second electrode portion, the narrow width part being configured to be disposed at a position where the first grasping member does not easily suffer a stress due to ultrasonic vibration when the living tissue is grasped between the second grasping member and the first grasping member, and to make a distance between the mutually opposed surfaces of the first electrode portion and the second electrode portion narrower than a distance at other positions.

Preferably, the narrow width part is a projecting electrode portion which is formed at a part of the second electrode portion in such a manner as to narrow a distance between the first electrode portion and the second electrode portion.

Preferably, the second electrode portion includes a metallic electrode body and a pad member which is formed of an insulator attached to the electrode body, and the pad member includes an engaging groove for alignment between the second electrode portion and the first electrode portion, the engaging groove being with the first electrode portion.

Preferably, the projecting electrode portion is a projection portion which is provided on that surface of the electrode body, which is opposed to the first electrode portion, so as to project toward the first electrode portion in such a manner as to narrow the distance between the first electrode portion and the second electrode portion in a state in which the first electrode portion is engaged in the engaging groove of the pad member, the projection portion forming a point of occurrence of a spark when the pad member is worn.

Preferably, the projection portion is configured such that a separate projection portion forming member is fixed to the electrode body.

Preferably, the projection portion is formed integral with the electrode body.

Preferably, the narrow width part is a projecting electrode portion which is formed at a part of the first electrode portion in such a manner as to narrow a distance between the first electrode portion and the second electrode portion.

Preferably, the second electrode portion includes a metallic electrode body and a pad member which is formed of an insulator attached to the electrode body, the pad member includes an engaging groove for alignment between the second electrode portion and the first electrode portion, the engaging groove being engaged with the first electrode portion, and the projecting electrode portion is a projection portion which is provided on that surface of the first electrode portion, which is opposed to the electrode body of the second electrode portion, so as to project toward the second electrode portion in such a manner as to narrow the distance between the first electrode portion and the second electrode portion in a state in which the first electrode portion is engaged in the engaging groove of the pad member.

Preferably, the first grasping member has a center axis, a distal end portion and a proximal end portion, the first electrode portion including a first curved-shaped portion which is curved relative to an axial direction of the center axis, and the second grasping member includes a second curved-shaped portion which is curved in a curved shape corresponding to the first curved-shaped portion.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 4 is a longitudinal cross-sectional view showing an internal structure of the transducer unit of the surgical operating apparatus according to the first embodiment;

FIG. 5A is a plan view showing a probe unit of the surgical operating apparatus according to the first embodiment;

FIG. 5B shows the relationship between the stress in the distal end portion of the probe unit and ultrasonic vibration characteristics;

FIG. 6 is a longitudinal cross-sectional view of a sheath unit of the surgical operating apparatus according to the first embodiment;

FIG. 7A is a plan view showing a driving pipe of the surgical operating apparatus according to the first embodiment;

FIG. 7B is a cross-sectional view taken along line 7B-7B in FIG. 7A;

FIG. 7C is a front view showing the driving pipe shown in FIG. 7B;

FIG. 8 is a side view showing, partly in cross section, an assembled state between the driving pipe and an insulation tube of the surgical operating apparatus according to the first embodiment;

FIG. 13 is a longitudinal cross-sectional view showing a coupled state between the jaw and the driving pipe of the surgical operating apparatus according to the first embodiment;

FIG. 14 is a cross-sectional view taken along line 14-14 in FIG. 13;

FIG. 15 is a plan view showing that surface of the jaw of the surgical operating apparatus according to the first embodiment, which is opposed to the probe distal end portion;

FIG. 16 is a transverse cross-sectional view taken along line 16-16 in FIG. 15, showing a closed state between the jaw and the probe of the surgical operating apparatus according to the first embodiment;

FIG. 17 is a transverse cross-sectional view of a spark point, taken along line 17-17 in FIG. 15, showing a closed state between the jaw and the probe of the surgical operating apparatus according to the first embodiment;

FIG. 18 is a longitudinal cross-sectional view showing a proximal end portion of the sheath unit of the surgical operating apparatus according to the first embodiment;

FIG. 19 is a cross-sectional view taken along line 19-19 in FIG. 18;

FIG. 20 is a cross-sectional view taken along line 20-20 in FIG. 18;

FIG. 21 is a longitudinal cross-sectional view showing a state before assembly of a knob member of the surgical operating apparatus according to the first embodiment;

DETAILED DESCRIPTION OF THE INVENTION

Figure 1:
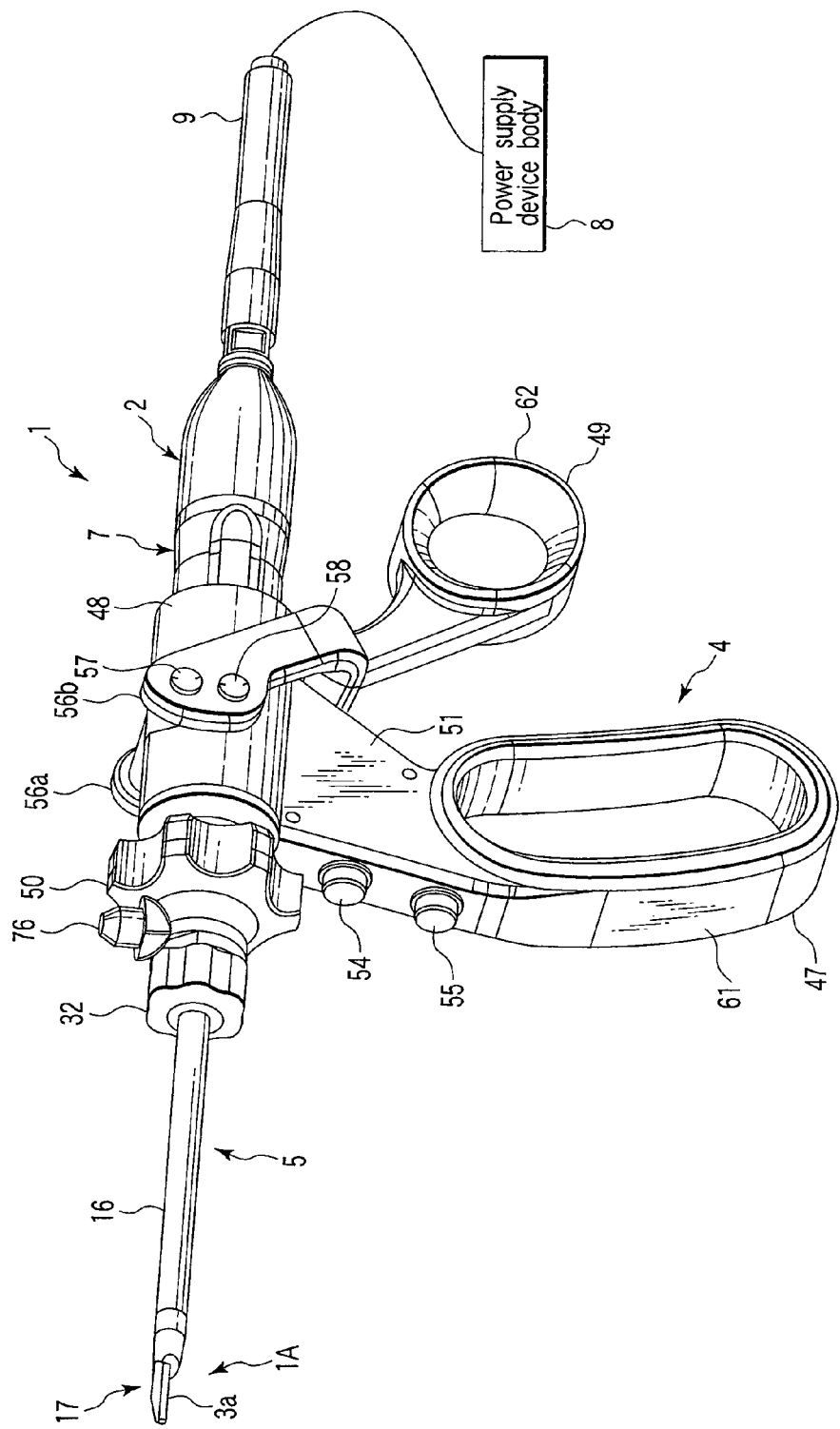
FIG. 1 is a perspective view that schematically shows the entire structure of a surgical operating apparatus according to a first embodiment of the present invention.

A first embodiment of the present invention will now be described with reference from FIG. 1 to FIG. 21. FIG. 1 schematically shows the entire structure of a handpiece 1 of an ultrasonic operating apparatus which is a surgical operating apparatus according to the first embodiment. The ultrasonic operating apparatus of the present embodiment is an ultrasonic coagulation/incision apparatus. This ultrasonic coagulation/incision apparatus can perform therapeutic treatment, such as incision, resection or coagulation, of a living tissue by making use of ultrasonic, and can also perform therapeutic treatment by high-frequency waves.

Figure 2:
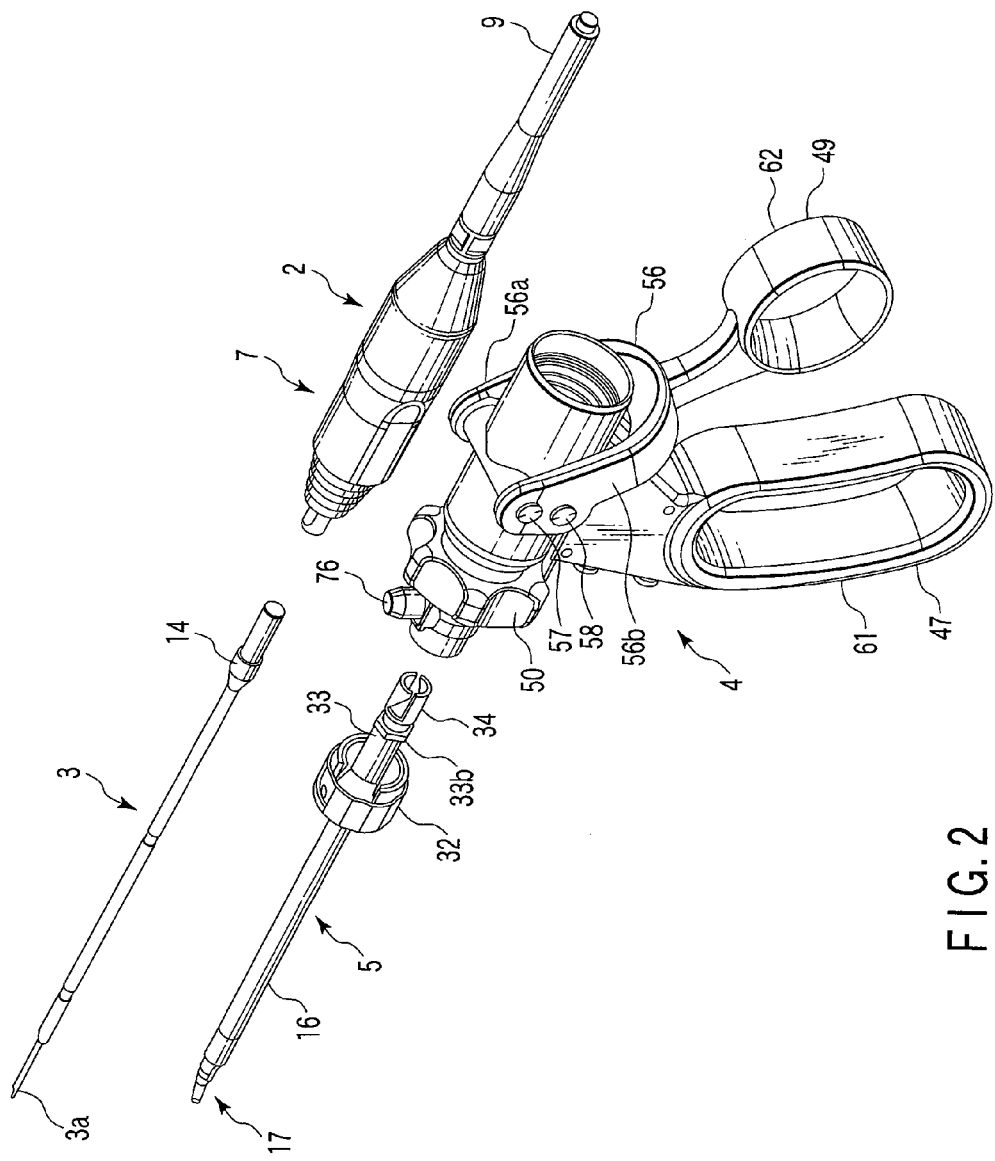
FIG. 2 is a perspective view showing a disassembled state of the surgical operating apparatus according to the first embodiment, with coupling sections of assembly units of the surgical operating apparatus being disconnected.

The handpiece 1, as shown in FIG. 2, comprises four units, namely, a transducer unit 2, a probe unit (probe section) 3, a handle unit (operation section) 4 and a sheath unit (sheath section) 5. These units are detachably coupled.

As shown in FIG. 4, an ultrasonic transducer 6 for generating ultrasonic vibration by a piezoelectric element, which converts an electric current to ultrasonic vibration, is built in the transducer unit 2. An outside of the ultrasonic transducer 6 is covered with a cylindrical transducer cover 7. As shown in FIG. 1, a cable 9, for supplying an electric current for generating ultrasonic vibration from a power supply device body 8, extends from a rear end of the transducer unit 2.

A proximal end portion of a horn 10, which increases the amplitude of ultrasonic vibration, is coupled to a front end portion of the ultrasonic transducer 6. A screw hole portion 10a for attachment of the probe is formed at a distal end portion of the horn 10.

FIG. 5A shows the external appearance of the entire probe unit 3. The probe unit 3 is designed such that the entire length thereof may become an integer number of times of half-wave length of the ultrasonic vibration. The probe unit 3 has a distal end portion and a proximal end portion, and includes a metallic rod-shaped vibration transmission member 11 having a long axis. A proximal end portion of the vibration transmission member 11 is provided with a screw portion 12 which is to be engaged with the screw hole portion 10a of the horn 10. The screw portion 12 is engaged with the screw hole portion 10a of the horn 10 of the transducer unit 2. Thereby, the probe unit 3 and the transducer unit 2 are assembled. At this time, a first high-frequency electric path 13, through which a high-frequency current is transmitted, is formed in the coupled body of the ultrasonic transducer 6 and the probe unit 3.

A probe distal end portion 3a is provided at a distal end portion of the vibration transmission member 11. A first grasping member is formed by the probe distal end portion 3a. The probe distal end portion 3a is formed in a substantially J-shaped curved form. The probe distal end portion 3a constitutes a first electrode section which is one of bipolar electrodes. The cross-sectional area of the probe unit 3 is decreased in the axial direction at several nodes of vibration in the axial direction, so that an amplitude necessary for therapeutic treatment can be obtained at the probe distal end portion 3a (see FIG. 5B). Rubber rings 3b, which are formed of elastic material in an annular shape, are attached to several positions of nodes of vibration along the axial direction of the probe unit 3. The rubber rings 3b prevent interference between the probe unit 3 and the sheath unit 5.

A flange portion 14 is provided at the position of the node of vibration on the most proximal end side in the axial direction of the probe unit 3. Engaging recess portions (not shown) each having a key groove shape are formed on the outer peripheral surface of the flange portion 14, for example, at three positions in the circumferential direction thereof.

FIG. 6 is a longitudinal cross-sectional view of the sheath unit 5. The sheath unit 5 includes a sheath body 16, which is formed of a circular cylindrical body, and a jaw 17 which is provided at a distal end of the sheath body 16. The sheath body 16 includes a metallic outer sheath 18 which is an outer cylinder, and a metallic driving pipe (driving member) 19 which is an inner cylinder (inner sheath). The driving pipe 19 is axially movably inserted in the outer sheath 18. FIGS. 7A to 7C and FIG. 8 show the driving pipe 19, and FIG. 9A to 9D show the outer sheath 18.

The outer peripheral surface of the outer sheath 18 is covered with an outer coating 18a which is formed of an insulating material such as a resin. An insulation tube 24, which is formed of an insulating material, is provided on the inner peripheral side of the driving pipe 19.

Figure 9A:
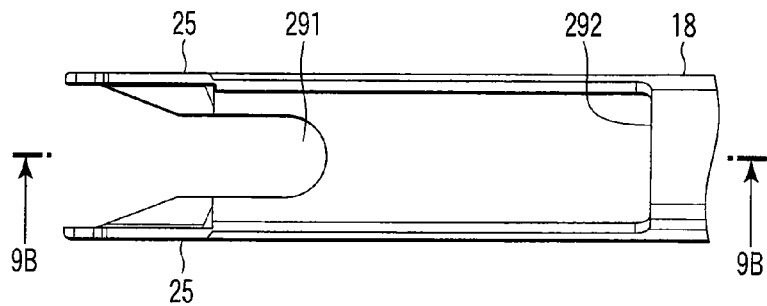
FIG. 9A is a longitudinal cross-sectional view showing a proximal end portion of an outer sheath of the sheath unit of the surgical operating apparatus according to the first embodiment.
Figure 9C:
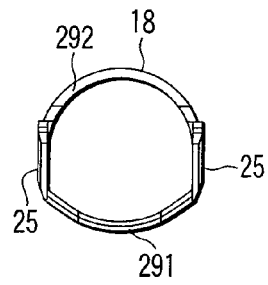
FIG. 9C is a front view showing the outer sheath shown in FIG. 9B.
Figure 9B:
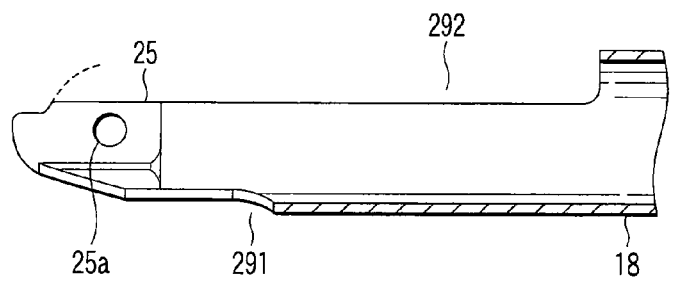
FIG. 9B is a cross-sectional view taken along line 9B-9B in FIG. 9A.
Figure 9D:
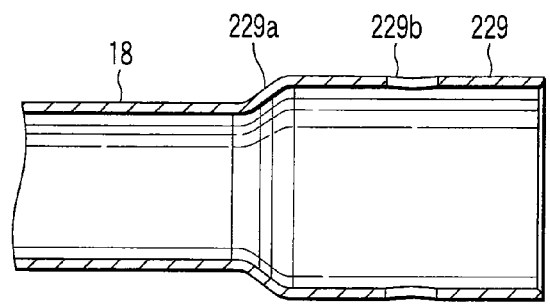
FIG. 9D is a longitudinal cross-sectional view showing a proximal end portion of the outer sheath.

As shown in FIG. 9A, a pair of left and right projection portions 25 are provided at a distal end portion of the outer sheath 18 so as to project in a forward direction of the outer sheath 18. As shown in FIG. 9B, a circular hole 25a is formed in each of the projection portions 25. A proximal end portion of the jaw 17 is rotatably attached to the circular poles 25a of the projection portions 25 via boss portions 27 (to be described later).

Further, a notch portion 292 for smoothing the movement of the driving pipe 19 is formed on an upper side (in FIG. 9B) of the distal end portion of the outer sheath 18. The notch portion 292 is formed to have a greater opening area than an opening portion 291 which is formed on a lower side (in FIG. 9B). As shown in FIG. 13, the notch portion 292 of the outer sheath 18 is covered with the outer coating 18a which is formed of an insulating material. When the probe unit 3 and the sheath unit 5 are assembled, the jaw 17 is positioned to be opposed to the probe distal end portion 3a of the probe unit 3.

FIG. 15 shows that surface of the jaw 17, which is opposed to the probe distal end portion 3a. As shown in FIG. 15, the jaw 17 is formed in a substantially J-shaped curved form, which corresponds to the curved shape of the probe distal end portion 3a, in accordance with the curved shape of the probe distal end portion 3a of the probe unit 3. A treatment section 1A of the handpiece 1 is constituted by the jaw 17 and the probe distal end portion 3a.

The jaw 17 includes a metallic jaw body 201 (see FIG. 10) which is an electrically conductive member, and a hold member 202 which is attached to the jaw body 201. The hold member 202 is composed of an electrode member 203 (see FIG. 11) for high-frequency treatment, and a pad member 204 (see FIG. 12) for ultrasonic therapeutic treatment. The electrode member 203 constitutes a second electrode section which is the other electrode of the bipolar electrodes. The pad member 204 is formed of an insulating material, for instance, a resin material such as polytetrafluoroethylene.

As shown in FIGS. 15 and 16, a groove portion 205, which is formed in accordance with the curved shape of the probe distal end portion 3a, is formed on the lower surface of the electrode member 203. The pad member 204 is inserted and mounted in the groove portion 205.

Inclined surfaces 205a, which are configured to gradually increase the groove width toward a lower-side opening surface, as shown in FIG. 16, are formed on both side wall surfaces of the groove portion 205. In addition, as shown in FIG. 15, tooth portions 203b for preventing a slip are formed on both side walls 203a of the groove portion 205 on the lower-side opening surface side. The tooth portions 203b form a slip-preventing section for preventing a slip of a grasped object between the probe distal end portion 3a and the jaw 17 when the jaw 17 and probe distal end portion 3a are engaged. A wall thickness T of the electrode member 203 is properly determined in consideration of the rigidity and coagulation performance.

Further, in the electrode member 203, a notch portion 205b is formed at a bottom portion of the inclined surface 205a of the groove portion 205. The notch portion 205b is formed in accordance with the curved shape of the probe distal end portion 3a. A push portion 207 of the pad member 204 is disposed at the notch portion 205b. The push portion 207 of the pad member 204 is a probe abutment member, on which the probe distal end portion 3a abuts, as shown in FIG. 16.

An alignment groove 207a is provided at a center of the push portion 207 of the pad member 204. As shown in FIG. 15, the alignment groove 207a is formed over the entire length of the pad member 204 from a front end portion to a rear end portion of the push portion 207. The probe distal end portion 3a is engaged in the alignment groove 207a. In the state in which the probe distal end portion 3a is engaged in the alignment groove 207a of the push portion 207, the probe distal end portion 3a is aligned and prevented from being displaced in the right-and-left direction (in FIG. 16) relative to the electrode member 203. Thereby, a clearance of a predetermined distance g1 is secured between the probe distal end portion 3a and the opposed inclined surface 205a of the electrode member 203, thus preventing contact between the inclined surfaces 205a of the electrode 203 and the probe distal end portion 3a.

The probe distal end portion 3a is formed to have a cross-sectional shape shown in FIG. 16. Specifically, left and right inclined surfaces 3a1, which are parallel to the left and right inclined surfaces 205a of the electrode member 203, are formed on the upper surface side of the probe distal end portion 3a. Left and right inclined surfaces 3a2, which are in opposite directions to the left and right inclined surfaces 3a1, are formed on the lower surface side of the probe distal end portion 3a. A flat surface portion 3a3, which is parallel to the alignment groove 207a of the push portion 207 of the pad member 204, is formed between the left and right inclined surfaces 3a1 on the upper surface side of the probe distal end portion 3a.

As shown in FIG. 17, projecting electrode portions 206 are formed on parts of the inclined surfaces 205a of the electrode member 203. The projecting electrode portions 206 project toward the opposed surfaces of the probe distal end portion 3a in the state in which the flat surface portion 3a3 at the upper surface of the probe distal end portion 3a is engaged in the alignment groove 207a of the push portion 207. Thereby, a gap g2 between the projecting electrode portion 206 and the probe distal end portion 3a is formed by a narrow width part, which is narrower than the distance g1 between those parts of the inclined surfaces 205a of the electrode member 203, which are other than the projecting electrode portions 206, and the probe distal end portion 3a. In short, the gap g2 of the narrow width part is formed to be g2<g1. The projecting electrode portions 206 are disposed at a position where the probe distal end portion 3a does not easily suffer a stress due to ultrasonic vibration when a living tissue is grasped between the inclined surfaces 205a of the electrode member 203 and the probe distal end portion 3a (see FIG. 5B).

Figure 11:
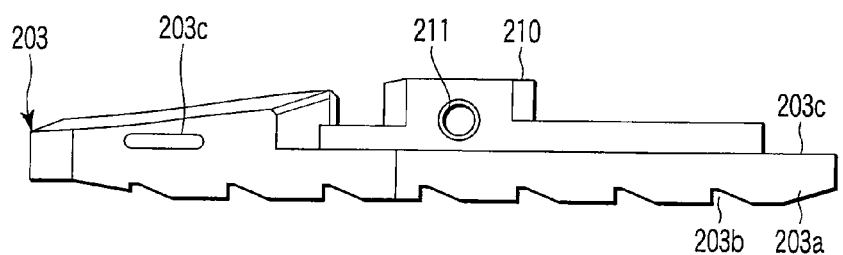
FIG. 11 is a side view showing an electrode member of the jaw of the surgical operating apparatus according to the first embodiment.
Figure 12:
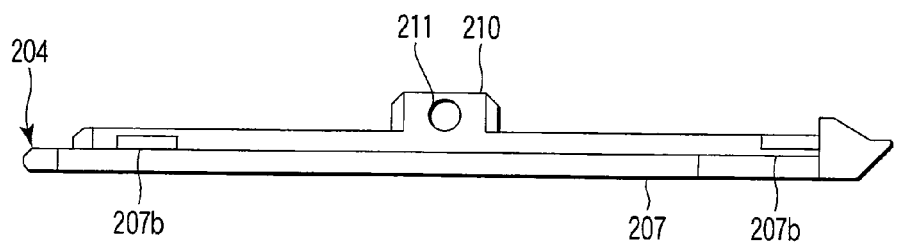
FIG. 12 is a side view showing a pad member of the jaw of the surgical operating apparatus according to the first embodiment.

As shown in FIG. 12, snap fit portions 207b are formed at a front end portion and a rear end portion of the push portion 207 of the pad member 204. As shown in FIG. 11, snap fit engaging portions 203c, which are disengageably engaged with the front and rear snap fit portions 207b of the pad member 204, are formed on the electrode member 203.

When the electrode member 203 and the pad member 204 are assembled, the snap fit portions 207b are engaged with the snap fit engaging portions 203c in the state in which the push portion 207 of the pad member 204 is inserted in the notch portion 205b of the groove portion 205 of the electrode member 203. Thereby, the electrode member 203 and the pad member 204 are integrally assembled and the hold member 202 is formed.

A projection portion 210 for attachment is projectingly provided on that side of the hold member 202, which is opposite to the surface thereof facing the probe distal end portion 3a. A screw insertion hole 211 is formed in the projection portion 210.

Figure 10:
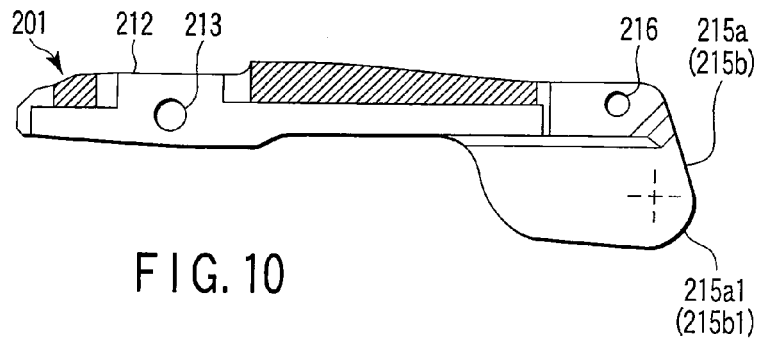
FIG. 10 is a side view showing a jaw body of a jaw of the surgical operating apparatus according to the first embodiment.

As shown in FIG. 10, a hold member engaging portion 212, which engages the projection portion 210 of the hold member 202, is provided on a distal end side of the jaw body 201. The projection portion 210 of the hold member 202 is engaged with the hold member engaging portion 212. Further, a screw hole 213 is formed in side wall portions of the hold member engaging portion 212. As shown in FIG. 13, when the hold member engaging portion 212 of the jaw body 201 and the projection portion 210 of the hold member 202 are engaged, a fixing screw 214, which is engaged in the screw hole 213 of the jaw body 201, is inserted in the screw insertion hole 211 of the hold member 202. In this state, the fixing screw 214 is fastened in the screw hole 213, and thereby the hold member 202 is attached to the jaw body 201. The electrode member 203 of the hold member 202 and the jaw body 201 are electrically connected via the fixing screw 214.

A proximal end portion of the jaw body 201 has two-forked arm portions 215a and 215b. The respective arm portions 215a and 215b have extension portions 215a1 and 215b1, which extend obliquely downward from the position of a center line of the jaw body 201. As shown in FIG. 14, the boss portions 27 are outwardly projectingly formed on outer surfaces of the extension portions 215a1 and 215b1. The boss portions 27 of the extension portions 215a1 and 215b1 are inserted and engaged in the circular holes 25a of the left and right projection portions 25 at the distal end portion of the outer sheath 18. Thereby, the jaw body 201 is rotatably attached by the boss portions 27 to the left and right projection portions 25 at the distal end portion of the outer sheath 18.

An operation pin insertion hole 216 is formed in a proximal portion of each of the two arm portions 215a and 215b. An operation pin 217 for coupling the jaw body 201 and the driving pipe 19 is inserted in the operation pin insertion holes 216. The jaw body 201 and the driving pipe 19 are electrically connected via the operation pin 217.

Thereby, the driving force of the driving pipe 19 is transmitted to the jaw 17 via the operation pin 217 by the advancing/retreating in the axial direction of the driving pipe 19. Accordingly, the jaw 17 is rotated about the boss portions 27. In this case, when the driving pipe 19 is pulled rearward, the jaw 17 is rotated about the boss portions 27 and driven (to an open position) in a direction away from the probe distal end portion 3a. Conversely, when the driving pipe 19 is pushed forward, the jaw 17 is rotated about the boss portions 27 and driven (to a closed position) in a direction toward the probe distal end portion 3a. A living tissue is held between the jaw 17 and the probe distal end portion 3a of the probe unit 3 when the jaw 17 is rotated to the closed position.

The treatment section 1A of the handpiece 1 is constituted by the jaw 17 and the probe distal end portion 3a of the probe unit 3. The treatment section 1A is configured to selectively perform a plurality of therapeutic functions, for example, two therapeutic functions (a first therapeutic function and a second therapeutic function) in this embodiment. For instance, the first therapeutic function is set to be a function of simultaneously outputting an ultrasonic therapeutic output and a high-frequency therapeutic output. The second therapeutic function is set to be a function of outputting only the high-frequency therapeutic output.

The first therapeutic function and second therapeutic function of the treatment section 1A are not limited to the above-described configuration. For example, the first therapeutic function may be set to be a function of outputting an ultrasonic therapeutic output in a maximum output state, and the second therapeutic function may be set to be a function of outputting the ultrasonic therapeutic output in a preset arbitrary output state which is lower than the maximum output state.

As shown in FIGS. 7A to 7C and FIG. 8, the driving pipe 19 includes a tubular body section 221 and an operating section 222. The body section 221 is inserted in the outer sheath 18 so as to be slidable in the axial direction of the outer sheath 18. The operating section 222 is disposed on the distal end side of the body section 221, and includes a connection section 223 which is connected to the jaw 17.

The peripheral wall of a tubular distal end portion of the body section 221 includes a crescent-shaped arcuate cross-sectional portion 224, which is formed by leaving a substantially crescent-shaped arcuate cross-sectional portion over a predetermined length along the axial direction, and cutting out the other portion. As shown in FIG. 7A, the arcuate cross-sectional portion 224 includes a taper portion 225 with a tapered distal end side, which is processed to gradually taper toward the distal end side. As shown in FIG. 7C, a U-shaped potion 226 having a U-shaped cross section is formed at a distal end of the taper portion 225. The operating section 222 is constituted by the U-shaped portion 226.

As shown in FIG. 7C, the U-shaped portion 226 has two side surfaces 226a and 226b, which are opposed to each other, and a connecting surface 226c which connects the two side surfaces 226a and 226b. The connection section 223 is formed in each of the two side surfaces 226a and 226b of the U-shaped portion 226.

As shown in FIG. 8, the insulation tube 24 includes a projection portion 228 which projects forward of the body section 221 of the driving pipe 19. The projection portion 228 extends up to a rear end position of the U-shaped portion 226.

Further, a proximal end portion of the insulation tube 24 extends to a proximal end side of the sheath body 16. The driving pipe 19 and probe unit 3 are electrically insulated by the insulation tube 24.

FIG. 18 shows a proximal end portion of the sheath body 16. The proximal end portion of the outer sheath 18 includes a flare portion 229 which has a greater inside diameter than the other portion (see FIG. 9D). A proximal end portion of the driving pipe 19 extends more rearward than the flare portion 229 of the outer sheath 18.

In addition, the proximal end portion of the sheath body 16 is provided with an attachment/detachment mechanism section 31 for attachment/detachment to/from the handle unit 4. The attachment/detachment mechanism section 31 includes a circular cylindrical large-diameter knob member 32, a guide cylindrical body (first tubular member) 33 which is formed of a metallic circular cylindrical body, and a circular cylindrical connection tube body (second tubular member) 34 which is formed of a resin material.

As shown in FIG. 19, the knob member 32 includes an annular knob body 32a. As shown in FIG. 20, the knob body 32a includes two C-shaped members 32a1 and 32a2 each having a substantially C shape. The two C-shaped members 32a1 and 32a2 are formed of a resin material, and the annular knob body 32a is formed in the state to which both end portions of the two C-shaped members 32a1 and 32a2 are coupled. The two C-shaped members 32a1 and 32a2 are coupled by two fixing screws 32b.

As shown in FIG. 21, engaging holes 301 are formed in inner peripheral surfaces of the two C-shaped members 32a1 and 32a2. Head portions 35a of pins 35, which restrict movement of internal parts, are engaged in the engaging holes 301. Thereby, the positions of the pins 35 can be restricted.

The guide cylinder 33 includes a tubular body 33a which is fitted over the flare portion 229 of the proximal end portion of the outer sheath 18 and extends rearwards. The distal end portion of the tubular body 33a is provided with a large-diameter portion 33b which has a greater outside diameter than the other portion. The knob member 32 is fitted on the large-diameter portion 33b. A connection flange portion 33c, which projects outward, is formed on the outer peripheral surface of a rear end portion of the guide cylinder 33.

Two pin insertion holes 33b1, which extend in the radial direction, are formed in the large-diameter portion 33b of the tubular body 33a. Shaft portion 35b of the pins 35 is inserted in the two pin insertion holes 33b1.

Two pin insertion holes are similarly formed in the flare portion 229 of the outer sheath 18 at positions corresponding to the two pin insertion holes 33b1 of the tubular body 33a. Shaft portions 35b of the pins 35 project inward through the two pin insertion holes 33b1 of the tuber body 33a and the two pin insertion holes of the outer sheath 18. Thereby, the knob member 32, the guide cylinder 33 and the flare portion 229 of the outer sheath 18 are integrally assembled by the pins 35 in the state in which the movement of the outer sheath 18 in the axial direction of the outer sheath 18 and the rotation thereof about the axis of the outer sheath 18 are restricted.

The connection tube body 34 is engaged in the guide cylinder 33 so as to be slidable in the axial direction of the outer sheath 18. The proximal end portion of the driving pipe 19 is inserted and fitted in the inner peripheral surface of the distal end portion of the connection tube body 34.

As shown in FIG. 18, a rotation restriction pin 235 is fixed on the proximal end portion of the driving pipe 19. As shown in FIG. 20, the rotation restriction pin 235 includes a large-diameter head portion 235a and a small-diameter shaft portion 235b. An engaging hole portion 302 for engagement with the head portion 235a of the rotation restriction pin 235 is formed in the connection tube body 34. A pin engaging hole 303 for engagement with the shaft portion 235b of the rotation restriction pin 235 is formed in the proximal end portion of the driving pipe 19. The driving pipe 19 and the connection tube body 34 are coupled via the rotation restriction pin 235. At this time, the driving pipe 19 and the connection tube body 34 are integrally assembled in the state in which the movement of the driving pipe 19 and the connection tube body 34 in the axial direction of the driving pipe 19 and the rotation of thereof about the axis of the driving pipe 19 are restricted by the rotation restriction pin 235.

The distal end portion of the connection tube body 34 is inserted into the inside of the flare portion 229 of the outer sheath 18 and extends to the vicinity of a stepped portion 229a between the outer sheath 18 and the flare portion 229.

Seal means 230 for effecting sealing between the outer sheath 18 and the driving pipe 19 is provided between the flare portion 229 and the driving pipe 19. The seal means 230 includes one backup ring 231 and one O ring 233. The O ring 233 is provided between the stepped portion 229a of the flare portion 229 and the backup ring 231 so as to be movable in the axial direction of the outer sheath 18. The position of the backup ring 231 of the O ring 233 is restricted at the distal end portion of the connection tube body 34. Further, the shape of the stepped portion 229a of the flare portion 229 is so used as to function as a front-side backup ring of the O ring 233. Thereby, only one backup ring 231 may be provided as the backup ring of the O ring 233.

The distal end portion of the connection tube body 34 has two slits 305 which extend along the axis of the driving pipe 19. Inner end portions of the shaft portions 35b of the pins 35 are inserted and engaged in the slits 30S. Thereby, the movement in the rotational direction of the three parts, namely, the guide cylinder 33, outer sheath 18 and connection tube body 34, relative to the knob member 32, can be restricted by the pin 35.

An attachment/detachment section 36 for attachment/detachment to/from the handle unit 4 is disposed at the rear end portion of the knob member 32. The attachment/detachment section 36 of the knob member 32 has a guide groove (not shown) with an inclined surface, and an engaging recess portion 42. The guide groove is provided extending in a circumferential direction on the outer peripheral surface of the proximal end portion of the knob member 32. In addition, the guide groove has a tapered inclined surface with an outside diameter gradually decreasing toward the rear end portion side of the knob member 32.

The engaging recess portion 42 is formed at one end portion of the guide groove. The engaging recess portion 42 is formed of a recess portion having a smaller diameter than the inclined surface of the guide groove. The engaging recess portion 42 is configured such that an engaging lever 43 (to be described later) on the handle unit 4 side is disengageably engaged in the engaging recess portion 42.

Figure 3:
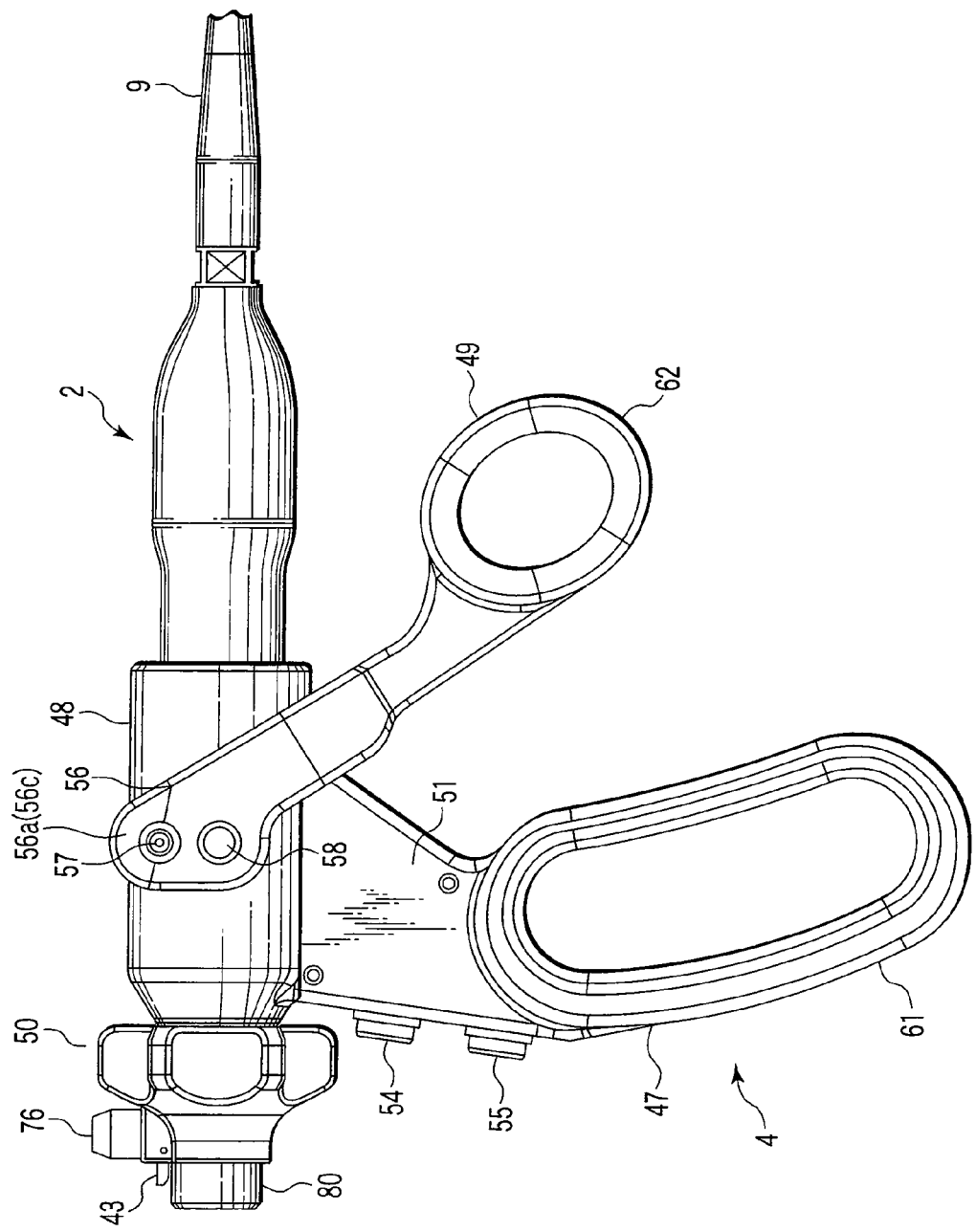
FIG. 3 is a side view showing a coupled state between a handle unit and a transducer unit of the surgical operating apparatus according to the first embodiment.

As shown in FIG. 3, the handle unit 4 mainly includes a stationary handle 47, a hold cylinder 48, a movable handle 49 and a rotational operation knob 50. The hold cylinder 48 is provided on the upper part of the stationary handle 47. A switch hold section 51 is provided between the stationary handle 47 and the hold cylinder 48.

As shown in FIG. 3, the switch hold section 51 has a switch attachment surface on a front side thereof, to which a plurality of hand switches, for example, two hand switches (first switch 54 and second switch 55) in the present embodiment, are attached. The first switch 54 and second switch 55 are switches for selecting therapeutic functions of the treatment section 1A of the handpiece 1.

In the switch hold section 51, the first switch 54 and second switch 55 are arranged in the up-and-down direction. The first switch 54 is disposed on an upper side of the switch hold section 51, and is set to be a switch which selects a first therapeutic function that is frequently used among the plural therapeutic functions. The second switch 55 is disposed on a lower side of the switch hold section 51, and is set to be a switch which selects another second therapeutic function of the plural therapeutic functions. For example, the first switch 54 is set to be a switch button for incision, and the second switch 55 is set to be a switch button for coagulation.

As shown in FIG. 2, the movable handle 49 has a substantially U-shaped arm section 56 at an upper part thereof. The U-shaped arm section 56 includes two arms 56a and 56b. The movable handle 49 is assembled to the hold cylinder 48 in the state in which the hold cylinder 48 is inserted between the two arms 56a and 56b.

Each of the arms 56a and 56b has a support pin 57 and an operation pin 58. A pin receiving hole portion (not shown) and a window portion (not shown) are formed in each of both side portions of the hold cylinder 48. The support pin 57 of each arm 56a, 56b is inserted in the pin receiving hole portion of the hold cylinder 48. Thereby, an upper end portion of the movable handle 49 is rotatably supported on the hold cylinder 48 via the support pins 57.

Ring-shaped finger hook portions 61 and 62 are provided on lower end portions of the stationary handle 47 and movable handle 49, respectively. By hooking the fingers on the finger hook portions 61 and 62 and holding them, the movable handle 49 rotates via the support pins 57 and the movable handle 49 is opened/closed relative to the stationary handle 47.

The operation pins 58 of the movable handle 49 extend into the hold cylinder 48 through the window portions of the hold cylinder 48. An operation force transmission mechanism (not shown), which transmits an operation force of the movable handle 49 to the driving pipe 19 of the jaw 17, is provided inside the hold cylinder 48.

If the movable handle 49 is held and the movable handle 49 is closed relative to the stationary handle 47, the operation pins 58 rotate about the support pins 57 in accordance with the rotational operation of the movable handle 49 at this time. A slider member (not shown) of the operation force transmission mechanism, which is in interlock with the rotation of the support pins 57, moves forward in the axial direction. At this time, the operation force of the movable handle 49 is transmitted to the connection tube body 34 of the sheath unit 5 via the operation force transmission mechanism, and the driving pipe 19 of the jaw 17 moves forward. Thereby, the jaw body 201 of the jaw 17 rotates via the boss portions 27.

Further, when a living tissue is grasped between the hold member 202 of the jaw 17 and the probe distal end portion 3a of the probe unit 3 by this operation, the hold member 202 rotates over a certain angle about the fixing screw 214 in accordance with the bending of the probe distal end portion 3a so that force uniformly acts over the entire length of the hold member 202. In this state, ultrasonic is output and a living tissue, such as a blood vessel, can be coagulated or incised.

The rotational operation knob 50 is fitted and fixed on the front end portion of the hold cylinder 48. The engaging lever 43 and an operation button 76 for operating the engaging lever 43 in such a direction as to release engagement of the engaging lever 43 are provided at the front end portion of the rotational operation knob 50.

Next, the operation of the present embodiment is described. The handpiece 1 of the ultrasonic operating apparatus of the present embodiment, as shown in FIG. 2, comprises four units, namely, the transducer unit 2, probe unit 3, handle unit 4 and sheath unit 5, which are detachable. When the handpiece 1 is used, the transducer unit 2 and the probe unit 3 are coupled. Thereby, the first high-frequency electric path 13, which transmits a high-frequency current to the coupled body of the transducer unit 2 and probe unit 3, is formed.

Subsequently, the handle unit 4 and the sheath unit 5 are coupled. When the handle unit 4 and sheath unit 5 are coupled, the connection tube body 34 is inserted in the hold cylinder 48 of the handle unit 4 in the state in which the knob member 32 of the sheath unit 5 is held. After this insertion operation, the knob member 32 of the sheath unit 5 is rotated about the axis, relative to the handle unit 4. By this operation, the engaging lever 43 on the handle unit 4 side is inserted and engaged in the engaging recess portion 42 of the knob member 32. Thereby, the sheath-unit-side electric path (not shown) and the handle-unit-side electric path are electrically connected. As a result, the second high-frequency electric path, which transmits a high-frequency current, is formed in the coupled body of the sheath unit 5 and handle unit 4.

When the sheath unit 5 is rotated about the axis thereof, the operation force on the handle unit 4 side at the time when the movable handle 49 is closed relative to the stationary handle 47 can be transmitted, at the same time, to the driving pipe 19 of the jaw 17 on the sheath unit 5 side. This state is the coupled state between the sheath unit 5 and the handle unit 4.

Thereafter, the coupled body of the sheath unit 5 and handle unit 4 and the coupled body of the ultrasonic transducer 6 and probe unit 3 are assembled as one body. In this assembling work, the second high-frequency electric path of the coupled body of the sheath unit 5 and handle unit 4 is connected to the wiring line for high-frequency power within the cable 9.

When the handpiece 1 is used, the movable handle 49 is opened/closed relative to the stationary handle 47. The driving pipe 19 is axially moved in interlock with the operation of the movable handle 49, and the jaw 17 is opened/closed, relative to the probe distal end portion 3*a* of the probe unit 3, in interlock with the advancing/retreating movement of the driving pipe 19 in its axial direction.

When the movable handle 49 is closed relative to the stationary handle 47, the driving pipe 19 is pushed forward in interlock with the operation of the movable handle 49. The jaw 17 is rotated and driven (to a closed position) in a direction toward the probe distal end portion 3*a* of the probe unit 3 in interlock with the pushing operation of the driving pipe 19. By the rotation of the jaw 17 to its closed position, a living tissue is held between the jaw 17 and the probe distal end portion 3*a* of the probe unit 3.

In this state, one of the switch button 54 for incision and the switch button 55 for coagulation, which are provided on the stationary handle 47, is selectively pressed. When the switch button 55 for coagulation is pressed, power is supplied to the first high-frequency electric path 13 for supplying a high-frequency current to the probe distal end portion 3*a* of the probe unit 3 and to the second high-frequency electric path for supplying a high-frequency current to the jaw body 28 of the sheath unit 5. Thereby, the two bipolar electrodes for high-frequency treatment are constituted by the probe distal end portion 3*a* of the probe unit 3 and the jaw body 28 of the sheath unit 5. By supplying a high-frequency current between the two bipolar electrodes which are constituted by the probe distal end portion 3*a* of the probe unit 3 and the jaw body 28 of the sheath unit 5, bipolar high-frequency treatment can be performed on the living tissue between the jaw 17 and the probe distal end portion 3*a* of the probe unit 3.

When the switch button 54 for incision is pressed, a driving current is supplied to the ultrasonic transducer 6 at the same time as the supply of high-frequency current, and the ultrasonic transducer 6 is driven. At this time, ultrasonic vibration from the ultrasonic transducer 6 is transmitted to the probe distal end portion 3*a* via the vibration transmission member 11. Thereby, incision, resection, etc. of the living tissue can be performed by making use of ultrasonic wave at the same time as the supply of high-frequency current. In the meantime, coagulation for the living tissue can be performed by using ultrasonic wave.

When the movable handle 49 is opened relative to the stationary handle 47, the driving pipe 19 is pulled to the proximal side in interlock with the opening operation of the movable handle 49. The jaw 17 is driven (to an open position) in a direction away from the probe distal end portion 3*a* of the probe unit 3 in interlock with the pulling operation of the driving pipe 19.

When the rotational operation knob 50 is rotated, the assembly unit within the hold cylinder 48 is rotated together with the rotational operation knob 50 as one body about the axis thereof. Further, the rotational operation force of the rotational operation knob 50 is transmitted to the vibration transmission member 11 of the probe unit 3. Thereby, the assembly unit within the hold cylinder 48 and the coupled body of the transducer unit 2 and probe unit 3 are rotated about the axis as one body.

At this time, the knob member 32 and guide cylindrical body 33 of the sheath unit 5 rotate together with the rotational operation knob 50. Furthermore, the outer sheath 18 rotates together with the guide cylindrical body 33, and the rotation of the guide cylindrical body 33 is transmitted to the connection tube body 34 and driving pipe 19 via the rotation restriction pin 235. Thus, the jaw 17 and probe distal end portion 3*a* of the treatment section 1A are rotated about the axis at the same time together with the rotational operation knob 50.

Figure 26:
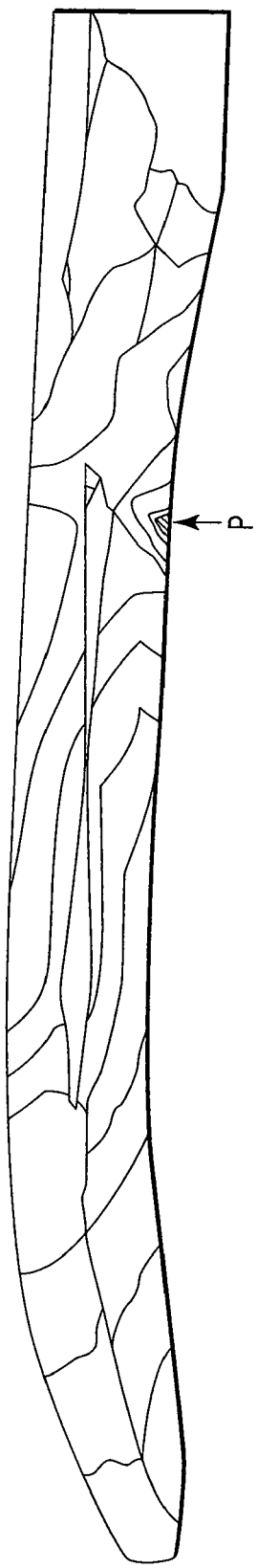
FIG. 26 is a characteristic diagram showing a distribution of the stress acting in a probe distal end portion which is formed in a substantially J-shaped curved form.

The following advantageous effects can be obtained with the above-described structure. Specifically, in the handpiece 1 of the ultrasonic operating apparatus of the present embodiment, the projecting electrode portions 206 are formed on the electrode member 203 of the jaw 17 of the treatment section 1A. The projecting electrode portions 206 project from the inclined surfaces 205*a* of the electrode member 203 toward the opposed surfaces of the probe distal end portion 3*a* in the state in which the probe distal end portion 3*a* is engaged in the alignment groove 207*a* of the push portion 207. Thereby, the gap g2 between the projecting electrode portion 206 and the probe distal end portion 3*a* is formed by the narrow width part, which is narrower than the distance g1 between those parts of the inclined surfaces 205*a* of the electrode member 203, which are other than the projecting electrode portions 206, and the probe distal end portion 3*a*. The projecting electrode portions 206 are formed at a position where the probe distal end portion 3*a* does not easily suffer a stress when a living tissue is grasped between the inclined surfaces 205*a* of the electrode member 203 and the probe distal end portion 3*a*. For example, the projecting electrode portions 206 are disposed at a position, such as a distal end side position of the probe distal end portion 3*a*, which is away from a proximal end side position of the curved shape (indicated by the arrow P in FIG. 26) where a stress due to ultrasonic vibration tends to concentrate.

Thus, when the pad member 204 is worn due to ultrasonic therapeutic treatment, the parts of the projecting electrode portions 206 can be first put in contact with the probe distal end portion 3*a*, and a spark can be occurred. As a result, the position of occurrence of a spark (the position where a crack occurs in the probe distal end portion 3*a*) can be controlled. Thereby, it becomes possible to surely prevent the occurrence of a spark at the proximal end side position of the curved shape (indicated by the arrow P in FIG. 26) where a stress due to ultrasonic vibration tends to concentrate. Therefore, a crack does not easily occur in the probe distal end portion 3*a*, and the durability can be improved. Moreover, in case a crack occurs in the probe distal end portion 3*a*, the crack can exactly be detected by the probe breakage detection section of the apparatus body.

The probe breakage detection section of the apparatus body is constituted as follows. Specifically, the probe breakage detection section detects the frequency of ultrasonic vibration. In general, the frequency of the probe+transducer is designed at a predetermined preset value, e.g. 47±1 kHz. As long as the frequency of ultrasonic vibration, which is detected by the probe breakage detection section, falls within the above range, ultrasonic vibration can be output. However, if a crack occurs in the probe, the frequency increases (the wavelength decreases), and the frequency falls out of the above range. Consequently, the body stops the output. However, if a crack occurs at a distal end side position of the curved shape of the probe distal end portion, the degree of increase of the frequency of ultrasonic vibration is small, and it becomes difficult for the probe breakage detection section to detect the broken state of the probe. In the present embodiment, as described above, the position where a spark occurs (the position where a crack occurs in the probe distal end portion 3a) can be controlled. Therefore, it is possible to surely prevent the occurrence of a spark at the distal end side position of the curved shape of the probe distal end portion. As a result, the safety can be ensured.

Besides, in the present embodiment, the alignment groove 207a is provided at a center of the push portion 207 of the pad member 204. Thus, the probe distal end portion 3a is engaged and fitted in the alignment groove 207a. By engaging the probe distal end portion 3a in the alignment groove 207a of the push portion 207, the probe distal end portion 3a can be prevented from being displaced in the right-and-left direction (in FIG. 16) relative to the electrode member 203. As a result, the clearance between the electrode member 203 and the probe distal end portion 3a can be exactly controlled.

Further, in the present embodiment, the boss portions 27 are outwardly projectingly formed on the arm portions 215a and 215b at the proximal end portion of the jaw body 201. The boss portions 27 are inserted and engaged in the circular holes 25a of the left and right projection portions 25 at the distal end portion of the outer sheath 18. Thereby, the jaw body 201 is rotatably attached by the boss portions 27 to the left and right projection portions 25 at the distal end portion of the outer sheath 18. Therefore, the number of parts can be reduced, compared to the case in which the proximal end portion of the jaw body 201 is connected to the distal end portion of the outer sheath 18 by separate parts such as pins. Thereby, the work of assembly between the jaw body 201 and the distal end portion of the outer sheath 18 can be facilitated.

In the present embodiment, as shown in FIG. 12, the snap fit portions 207b are formed at the front end portion and the rear end portion of the push portion 207 of the pad member 204. As shown in FIG. 11, the snap fit engaging portions 203c are formed on the electrode member 203. When the electrode member 203 and the pad member 204 are assembled, the snap fit portions 207b are engaged with the snap fit engaging portions 203c. Thereby, the electrode member 203 and the pad member 204 are integrally assembled. Therefore, the work of assembly between the electrode member 203 and the pad member 204 can be made easier than in the prior art.

In the present embodiment, as shown in FIG. 20, in the knob member 32 at the proximal end portion of the sheath body 16, the two C-shaped members 32a1 and 32a2 each having a substantially C shape are coupled by the two fixing screws 32b, and thus the annular knob body 32a is formed as shown in FIG. 19. Further, the engaging holes 301 are formed in inner peripheral surfaces of the two C-shaped members 32a1 and 32a2. The head portions 35a of the pins 35, which restrict movement of internal parts, are engaged in the engaging holes 301. Thereby, the positions of the pins 35 can be restricted. Therefore, the number of internal parts assembled in the knob member 32 can be made less than in the prior art, and the assembly can be made easier.

In the present embodiment, since the position of the backup ring 231 of the O ring 233 is restricted at the distal end portion of the connection tube body 34, there is no need to provide other parts for restricting the position of the backup ring 231. Therefore, the number of parts can be reduced and the assembly can be made easier.

In the present embodiment, the movement of the three parts, namely, the knob member 32, the guide cylinder 33 and the flare portion 229 of the outer sheath 18 in the axial direction of the outer sheath 18 and the movement thereof about the axis of the outer sheath 18 are restricted by the pins 35. Thereby, compared to the prior art, the number of parts can be reduced and the assembly can be made easier.

In the present embodiment, the stepped portion 229a between the outer sheath 18 and the flare portion 229 can be made to serve also as a front-side backup ring of the O ring 233. Thus, it should suffice to provide only one backup ring 231 on the rear side of the O ring 233. Thereby, compared to the case in which backup rings are provided in front of and behind the O ring 233, the number of parts can be reduced and the assembly can be made easier.

In the present embodiment, the diameter of the head portion 235a of the rotation restriction pin 235, which couples between the driving pipe 19 and connection tube body 34 and restricts the axial movement of the driving pipe 19 and the rotation of the driving pipe 19 about its axis, is increased. Thereby, swinging of the head portion 235a of the rotation restriction pin 235 can be prevented.

Further, in the present embodiment, the notch portion 292 for smoothing the movement of the driving pipe 19 is formed on the upper side (in FIG. 9B) of the distal end portion of the outer sheath 18. When the jaw 17 is rotated, the coupling portion between the connection section 223 of the U-shaped portion 226 of the driving pipe 19 and the operation pin 217 of the jaw 17 makes arcuate movement. Consequently, the U-shaped portion 226 of the driving pipe 19 moves up and down. At this time, when the U-shaped portion 226 of the driving pipe 19 moves upward, the notch portion 292 at the distal end portion of the outer sheath 18 can prevent contact between the outer sheath 18 and the driving pipe 19. Therefore, when the U-shaped portion 226 of the driving pipe 19 moves upward, it is possible to prevent occurrence of frictional force due to contact between the outer sheath 18 and the driving pipe 19, which leads to non-smooth sliding movement. As a result, the rotational operation of the jaw 17 can smoothly be performed.

In the present embodiment, there is no need to form a slit in the U-shaped portion 226 of the driving pipe 19. Accordingly, a decrease in strength of the U-shaped portion 226 of the driving pipe 19 can be prevented.

In the present embodiment, as shown in FIG. 13, the notch portion 292 of the outer sheath 18 is covered with the outer coating 18a which is formed of an insulating material. Thus, it is possible to prevent the notch portion 292 of the outer sheath 18 from being caught by, for instance, a trocar.

Figure 22:
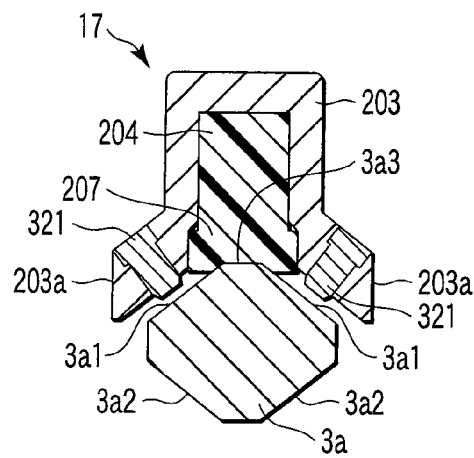
FIG. 22 is a transverse cross-sectional view showing a spark point between a jaw and a probe of a surgical operating apparatus according to a second embodiment of the present invention.

FIG. 22 shows a second embodiment of the present invention. In this embodiment, the structure of the jaw 17 in the first embodiment is altered as follows. Specifically, separate pin-shaped projection portion forming members 321 are fixed to the left and right inclined surfaces 205a, which are formed on both side walls 203a of the groove portion 205 in the electrode member 203 of the jaw 17, thereby forming projecting electrode portions. The projection portion forming members 321 are fixed to both side walls 203a of the electrode member 203 by means of, e.g. screwing or laser welding. Distal end portions of the projection portion forming members 321 project toward the left and right inclined surfaces 3a1 which are opposed surfaces of the probe distal end portion 3a. Thereby, the gap g2 (see FIG. 17) between the distal end of the projection portion forming member 321 and the probe distal end portion 3a is formed by a narrow width part, which is narrower than the distance g1 between those parts of the inclined surfaces 205a of the electrode member 203, which are other than the projecting electrode portions 206, and the left and right inclined surfaces 3a1 of the probe distal end portion 3a.

The following advantageous effects can be obtained with the above-described structure. Specifically, in the handpiece 1 of the ultrasonic operating apparatus according to the present embodiment, the separate pin-shaped projection portion forming members 321 are fixed to the electrode member 203 of the jaw 17 of the treatment section 1A, thereby forming the projecting electrode portions. The projection portion forming members 321 project from the left and right inclined surfaces 205a of the electrode member 203 toward the left and right inclined surfaces 3a1 of the probe distal end portion 3a in the state in which the flat surface portion 3a3 of the probe distal end portion 3a is engaged in the alignment groove 207a of the push portion 207. Thereby, the gap g2 between the projecting electrode portion 206 and the probe distal end portion 3a is formed by the narrow width part, which is narrower than the distance g1 between those parts of the inclined surfaces 205a of the electrode member 203, which are other than the projection portion forming members 321, and the probe distal end portion 3a. The projection portion forming members 321 are formed at a position where the probe distal end portion 3a does not easily suffer a stress when a living tissue is grasped between the inclined surfaces 205a of the electrode member 203 and the probe distal end portion 3a. For example, the projection portion forming members 321 are disposed at a position, such as a distal end side position of the probe distal end portion 3a, which is away from a proximal end side position of the curved shape (indicated by the arrow P in FIG. 26) where a stress due to ultrasonic vibration tends to concentrate.

Thus, when the pad member 204 is worn due to ultrasonic therapeutic treatment, the parts of the projection portion forming members 321 can be first put in contact with the probe distal end portion 3a, and a spark can be occurred. As a result, the position of occurrence of a spark (the position where a crack occurs in the probe distal end portion 3a) can be controlled. Thereby, it becomes possible to surely prevent the occurrence of a spark at the proximal end side position of the curved shape (indicated by the arrow P in FIG. 26) where a stress due to ultrasonic vibration tends to concentrate. Therefore, a crack does not easily occur in the probe distal end portion 3a, and the durability can be improved. Moreover, in case a crack occurs in the probe distal end portion 3a, the crack can exactly be detected by the probe breakage detection section of the apparatus body. As a result, the safety can be ensured.

Figure 23:
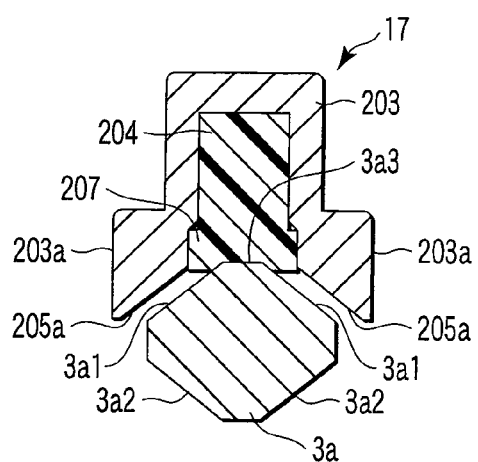
FIG. 23 is a transverse cross-sectional view showing a closed state between a jaw and a probe of a surgical operating apparatus according to a third embodiment of the present invention.
Figure 24:
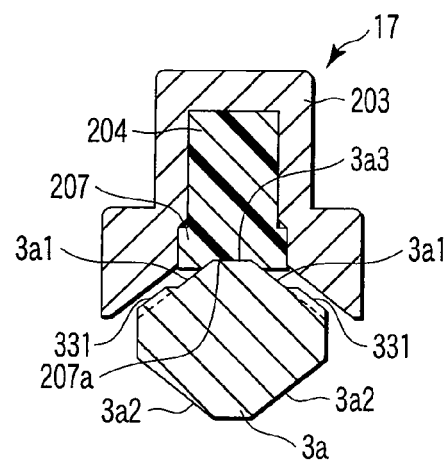
FIG. 24 is a transverse cross-sectional view showing a spark point between the jaw and the probe of the surgical operating apparatus according to the third embodiment.

FIG. 23A to FIG. 25 show a third embodiment of the present invention. In this embodiment, the structure of the jaw 17 in the first embodiment is altered as follows. Specifically, in the present embodiment, as shown in FIG. 23A to 23C, projecting electrode portions 331 are formed on the upper-side left and right inclined surfaces 3a1 of the probe distal end portion 3a.

Figure 25C:
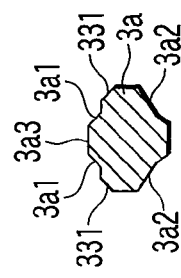
FIG. 25C is a cross-sectional view taken along line 25C-25C in FIG. 25B.
Figure 25A:
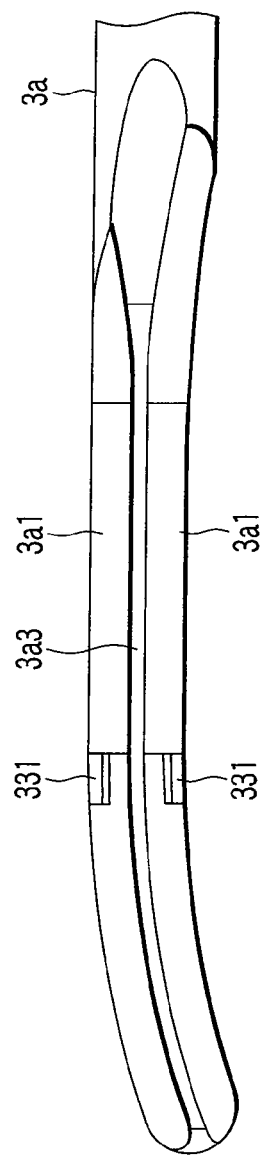
FIG. 25A is a plan view showing that surface of a probe distal end portion of the surgical operating apparatus according to the third embodiment, which is opposed to an electrode member of the jaw.
Figure 25B:
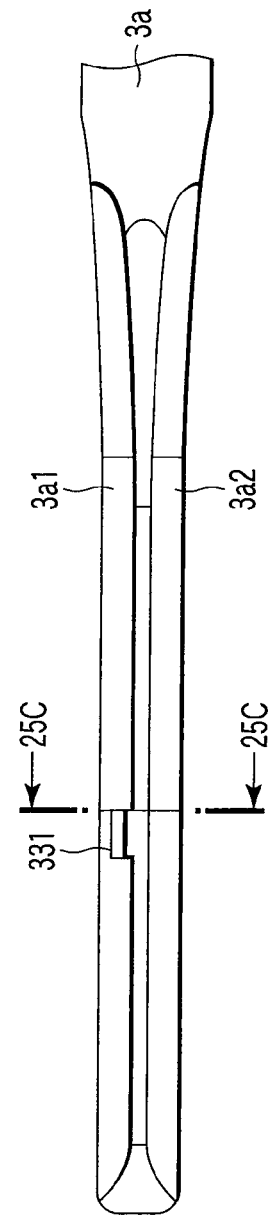
FIG. 25B is a side view of the probe distal end portion of the surgical operating apparatus according to the third embodiment.

As shown in FIG. 25, distal ends of the projecting electrode portions 331 of the probe distal end portion 3a project toward the left and right inclined surfaces 205a of the electrode member 203. Thereby, the gap g2 (see FIG. 17) between the distal ends of the projecting electrode portions 331 and the left and right inclined surfaces 205a of the electrode member 203 is formed by a narrow width part, which is narrower than the distance g1 between those parts of the probe distal end portion 3a, which are other than the projecting electrode portions 331, and the inclined surfaces 205a of the electrode member 203.

The following advantageous effects can be obtained with the above-described structure. Specifically, in the handpiece 1 of the ultrasonic operating apparatus according to the present embodiment, the projecting electrode portions 331 are formed on the upper-side left and right inclined surfaces 3a1 of the probe distal end portion 3a of the treatment section 1A. Thereby, the gap g2 between the projecting electrode portions 331 and the left and right inclined surfaces 205a of the electrode member 203 is formed by the narrow width part, which is narrower than the distance g1 between the inclined surfaces 205a of the electrode member 203 and the parts other than the projecting electrode portions 331. The projecting electrode portions 331 are formed at a position where the probe distal end portion 3a does not easily suffer a stress when a living tissue is grasped between the inclined surfaces 205a of the electrode member 203 and the probe distal end portion 3a. For example, the projecting electrode portions 331 are disposed at a position, such as a distal end side position of the probe distal end portion 3a, which is away from a proximal end side position of the curved shape (indicated by the arrow P in FIG. 26) where a stress due to ultrasonic vibration tends to concentrate.

Thus, when the pad member 204 is worn due to ultrasonic therapeutic treatment, the parts of the projecting electrode portions 331 can be first put in contact with the left and right inclined surfaces 205a of the electrode member 203, and a spark can be occurred. As a result, the position of occurrence of a spark (the position where a crack occurs in the probe distal end portion 3a) can be controlled. Thereby, it becomes possible to surely prevent the occurrence of a spark at the proximal end side position of the curved shape (indicated by the arrow P in FIG. 26) where a stress due to ultrasonic vibration tends to concentrate. Therefore, a crack does not easily occur in the probe distal end portion 3a, and the durability can be improved. Moreover, in case a crack occurs in the probe distal end portion 3a, the crack can exactly be detected by the probe breakage detection section of the apparatus body. As a result, the safety can be ensured.

Needless to say, the present invention is not limited to the above-described embodiments, and various modifications may be made without departing from the spirit of the invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:
1. A surgical operating apparatus comprising:
an ultrasonic treatment section configured to perform ultrasonic treatment on a treatment object; and
a high-frequency treatment section configured to perform high-frequency treatment on the treatment object,
wherein the ultrasonic treatment section comprises:
a first grasping member;
a second grasping member which is provided to be openable/closable relative to the first grasping member, the first grasping member and the second grasping member being configured to grasp the treatment object between them;
an ultrasonic vibration portion which is provided in the first grasping member and which is connected to an ultrasonic transducer; and
a push portion which is provided on the second grasping member, and which is opposed to the ultrasonic vibration portion, the push portion being configured to push the treatment object between the push portion and the ultrasonic vibration portion,
the ultrasonic treatment section is configured to
perform the ultrasonic treatment on the treatment object between the ultrasonic vibration portion and the push portion, the high-frequency treatment section comprises:
a first electrode portion which is provided on the first grasping member, and which includes a first surface opposed to the second grasping member; and
a second electrode portion which is provided on the second grasping member, and which includes a second surface opposed to the first surface of the first grasping member, the second electrode portion and the first electrode portion being configured to perform high-frequency treatment on the treatment object grasped between the second electrode portion and the first gasping member, and
at least one of the first surface of the first electrode portion and the second surface of the second electrode portion includes a narrowing width section disposed at a narrowing position different from a stress concentrating position where a stress due to ultrasonic vibration tends to concentrate in the first grasping member with respect to a longitudinal direction when the treatment object is grasped between the second grasping member and the first grasping member, the narrowing width section being configured to make a distance between the first surface and the second surface at the narrowing position narrower than a distance between the first surface and the second surface at positions other than the narrowing position.

2. The surgical operating apparatus according to claim 1, wherein the narrowing width section includes a projecting electrode portion which is provided to the second electrode portion, and which projects toward the first surface of the first electrode portion, the projecting electrode portion being configured to narrow a distance between the first electrode portion and the second electrode portion at the narrowing position.

3. The surgical operating apparatus according to claim 2, wherein the second electrode portion includes a metallic electrode body and a pad member which is formed of an insulator attached to the electrode body, and
the pad member includes an engaging groove for alignment between the second electrode portion and the first electrode portion, the engaging groove being engaged with the first electrode portion.

4. The surgical operating apparatus according to claim 3, wherein the projecting electrode portion is a projection portion which is opposed to the first electrode portion, and which projects from the electrode body toward the first surface of the first electrode portion, the projection portion being configured to narrow the distance between the first electrode portion and the second electrode portion at the narrowing position in a state when the first electrode portion is engaged in the engaging groove of the pad member, and the projection portion being configured to form a spark point at the narrowing position by firstly contacting with the first surface of the first electrode portion at the narrowing position when the distance between the first electrode portion and the second electrode is decreased due to wear of the pad member.

5. The surgical operating apparatus according to claim 4, wherein the projection portion is configured such that a separate projection portion forming member is fixed to the electrode body.

6. The surgical operating apparatus according to claim 4, wherein the projection portion is formed integral with the electrode body.

7. The surgical operating apparatus according to claim 1, wherein the narrowing width section includes a projecting electrode portion which is provided to the first electrode portion, and which projects toward the second surface of the second electrode portion, the projecting electrode portion being configured to narrow a distance between the first electrode portion and the second electrode portion at the narrowing position.

8. The surgical operating apparatus according to claim 7, wherein the second electrode portion includes a metallic electrode body and a pad member which is formed of an insulator attached to the electrode body,
the pad member includes an engaging groove for alignment between the second electrode portion and the first electrode portion, the engaging groove being engaged with the first electrode portion, and
the projecting electrode portion is a projection portion which is opposed to the electrode body of the second electrode portion, and which projects from the first electrode portion toward the second surface of the second electrode portion, the projection portion being configured to narrow the distance between the first electrode portion and the second electrode portion at the narrowing position in a state when the first electrode portion is engaged in the engaging groove of the pad member.

9. The surgical operating apparatus according to claim 1, wherein the first grasping member has a center axis, a distal end portion and a proximal end portion, the first electrode portion including a first curved-shaped portion which is curved relative to an axial direction of the center axis, and
the second grasping member includes a second curved-shaped portion which is curved in a curved shape corresponding to the first curved-shaped portion.

* * * * *